United States Patent
Brotherton-Pleiss et al.

(10) Patent No.: US 7,491,821 B2
(45) Date of Patent: Feb. 17, 2009

(54) INHIBITORS OF P2X$_3$

(75) Inventors: Christine E. Brotherton-Pleiss, Sunnyvale, CA (US); Michael Patrick Dillon, San Francisco, CA (US); Shelley K. Gleason, Redwood City, CA (US); Clara Jeou Jen Lin, Palo Alto, CA (US); Ryan Craig Schoenfeld, San Jose, CA (US); Marzia Villa, Sunnyvale, CA (US); Yansheng Zhai, East Palo Alto, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 109 days.

(21) Appl. No.: 11/502,797

(22) Filed: Aug. 11, 2006

(65) Prior Publication Data
US 2007/0037974 A1 Feb. 15, 2007

Related U.S. Application Data

(60) Provisional application No. 60/708,722, filed on Aug. 15, 2005.

(51) Int. Cl.
C07D 403/12 (2006.01)
C07D 413/12 (2006.01)
C07D 417/12 (2006.01)
C07D 295/194 (2006.01)

(52) U.S. Cl. ............ 544/295; 544/121; 544/357; 544/364; 544/369; 544/371; 544/386; 544/391; 544/362; 544/237; 544/250; 544/330; 544/331; 546/209; 546/212; 546/214

(58) Field of Classification Search .......... 544/295, 544/369; 514/254.02, 252.19
See application file for complete search history.

(56) References Cited

U.S. PATENT DOCUMENTS

| | | | |
|---|---|---|---|
| 3,705,899 A | 12/1972 | Regnier et al. | |
| 5,696,267 A | 12/1997 | Reichard et al. | |
| 5,840,725 A | 11/1998 | Reichard et al. | |
| 5,945,428 A | 8/1999 | Shih et al. | |
| 5,985,603 A | 11/1999 | Valera et al. | |
| 6,133,434 A | 10/2000 | Buell et al. | |
| 6,194,162 B1 | 2/2001 | Valera et al. | |
| 6,239,134 B1 | 5/2001 | Sabb et al. | |
| 2003/0083359 A1 | 5/2003 | Lee et al. | |
| 2004/0023203 A1 | 2/2004 | Miesenbock et al. | |
| 2004/0029887 A1 | 2/2004 | Bhatia et al. | |
| 2004/0067967 A1 | 4/2004 | Barden et al. | |

FOREIGN PATENT DOCUMENTS

| EP | 0 395 313 A2 | 4/1990 |
|---|---|---|
| EP | 0 462 638 A1 | 12/1991 |
| EP | 0 709 375 A2 | 5/1996 |
| EP | 0 474 561 B1 | 12/1998 |
| GB | 2 303 303 A | 2/1997 |
| JP | 61 100566 A | 5/1986 |

(Continued)

OTHER PUBLICATIONS

Drugarin et al. Chemical Abstracts, vol. 96, No. 85515 (1982).*

(Continued)

*Primary Examiner*—Emily Bernhardt
(74) *Attorney, Agent, or Firm*—Grant D. Green

(57) ABSTRACT

Compounds of formula 1 are modulators of P2X3 useful for the treatment of pain and genitourinary, gastrointestinal, and respiratory disorders:

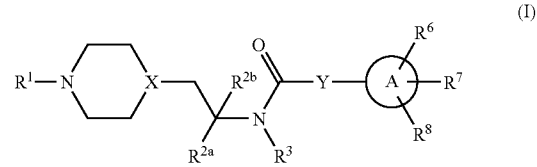

(I)

wherein

R$^1$ is —C(=S)CH$_3$, pyridyl, pyrimidinyl, pyrazinyl, thiazolyl, furyl, furylcarbonyl, acetyl, or carbamoyl; R$^{2a}$ and R$^{2b}$ are independently H, methyl, or ethyl; R$^3$ is H or methyl; Y is a bond, —(CR$^4$R$^5$)$_n$— or —CR$^4$=CR$^5$—; wherein R$^4$ and R$^5$ are each independently H or methyl and n is 1 or 2; X is N or CH; A is phenyl, 5-membered heterocyclyl, or 6-membered heterocyclyl; R$^6$, R$^7$ and R$^8$ are each independently H, halo, lower alkyl, cycloalkyl, alkylthio, alkylthio-lower alkyl, alkylsulfonyl-lower alkyl, di(lower alkyl)amino-lower alkyl, morpholinyl-lower alkyl, 4-methyl-piperazinyl-methyl, trifluoromethyl, pyridyl, tetrazolyl, thiophenyl, phenyl, biphenyl, or benzyl (where thiophenyl, phenyl and benzyl are substituted with 0-3 lower alkyl, halo, sulfonamido, trifluoromethyl, lower alkoxy or lower alkylthio) or R$^6$ and R$^7$ together form a 5-membered or 6-membered carbocyclic or heterocyclic ring substituted with 0-3 substituents selected from the group consisting of lower alkyl, lower alkoxy, oxo, halo, thiophenyl-lower alkyl, phenyl, benzyl (where phenyl and benzyl are substituted with 0-3 lower alkyl, halo, sulfonamido, trifluoro-methyl, lower alkoxy, lower alkylthio, amino-lower alkyl, lower alkylamino-lower alkyl, or di(lower alkyl)amino-lower alkyl); and pharmaceutically acceptable salts thereof; wherein when R$^1$ is pyrimidin-2-yl, X is N, Y is a bond and A is oxazol-5-yl the carbon atom at position 4 in said oxazol-5-yl is not substituted by propyl when the carbon atom at position 2 in said oxazol-5-yl is substituted by substituted phenyl and the carbon atom at position 4 in said oxazol-5-yl is not substituted by phenyl when the carbon atom at position 2 is substituted by unsubstituted or substituted phenyl.

15 Claims, No Drawings

FOREIGN PATENT DOCUMENTS

| | | |
|---|---|---|
| WO | WO 99/03833 | 1/1999 |
| WO | WO 00/51999 A1 | 9/2000 |
| WO | WO 00/52002 A1 | 9/2000 |
| WO | WO 00/63379 A2 | 10/2000 |
| WO | WO 02/094767 A2 | 11/2002 |
| WO | WO 02/094767 A3 | 11/2002 |
| WO | WO 03/099266 A2 | 12/2003 |
| WO | WO 03/099266 A3 | 12/2003 |

OTHER PUBLICATIONS

Bian, X., et al "Peristalsis is impaired in the small intestine of mice lacking the $P2X_3$ subunit", *J. Physiol* (2003) 551.1, 309-322.

Brouns, I., eg al, "Intraepithelial Vagal Sensory Nerve Terminals in Rat Pulmonary Neuroepithelial Bodies Express $P2X_3$ Receptors", *Am. J. Respir. Cell Mol. Biol.* (2000) vol. 23, 52-61.

King, B.F., et al., "Antagonism of ATP responses at P2X receptor subtypes by the pH indicator dye, Phenol red" *Brit Jnl Pharm* (2005) 145, 313-322.

Rong, W., et al., "Pivotal Role of Nucleotide $P2X_2$ Receptor Subunit of the ATP-Gated Ion Channel Mediating Ventilatory Responses to Hypoxia", *Jnl Neuroscience*, (Dec. 10, 2003) 23(36), 11314-11321.

Wynn, G., et al., "Purinergic component of mechanosensory transduction is increased in a rat model of colitis", *AJP-Gastro Liver Physio*, (2004) 287:647-657.

Yiangou, Y., et al., "ATP-gated ion channel P2X3 is increased in human inflammatory bowel disease", *Neurogastroenterol Mot.*, (2001) 13, 365-369.

C. Drugarin et al., "Synthese ellniger neuer Piperazinderivate", Pharmazie (1981) 36:709-10.

* cited by examiner

US 7,491,821 B2

INHIBITORS OF P2X₃

RELATED APPLICATIONS

This application claims priority from U.S. Ser. No. 60/708,722, filed Aug. 15, 2005, incorporated herein by reference in full.

FIELD OF THE INVENTION

This invention pertains to compounds useful for treatment of diseases associated with P2X purinergic receptors, and more particularly to P2X$_3$ antagonists usable for treatment of genitourinary, gastrointestinal, respiratory, and pain-related diseases, conditions and disorders.

BACKGROUND OF THE INVENTION

The urinary bladder is responsible for two important physiological functions: urine storage and urine emptying. This process involves two main steps: (1) the bladder fills progressively until the tension in its walls rises above a threshold level; and (2) a nervous reflex, called the micturition reflex, occurs that empties the bladder or, if this fails, at least causes a conscious desire to urinate. Although the micturition reflex is an autonomic spinal cord reflex, it can also be inhibited or mediated by centers in the cerebral cortex or brain.

Purines, acting via extracellular purinoreceptors, have been implicated as having a variety of physiological and pathological roles. (See, G. Burnstock, *Drug Dev. Res.* (1993) 28:195-206.) ATP, and to a lesser extent, adenosine, can stimulate sensory nerve endings resulting in intense pain and a pronounced increase in sensory nerve discharge. ATP receptors have been classified into two major families, the P2Y- and P2X-purinoreceptors, on the basis of molecular structure, transduction mechanisms, and pharmacological characterization. The P2Y-purinoreceptors are G-protein coupled receptors, while the P2X-purinoreceptors are a family of ATP-gated cation channels. Purinergic receptors, in particular, P2X receptors, are known to form homomultimers or heteromultimers. To date, cDNAs for several P2X receptors subtypes have been cloned, including: six homomeric receptors, P2X$_1$; P2X$_2$; P2X$_3$; P2X$_4$; P2X$_5$; and P2X$_7$; and three heteromeric receptors P2X$_{2/3}$, P2X$_{4/6}$, P2X$_{1/5}$ (See, e.g., C. C. Chen et al., *Nature* (1995) 377:428-31; C. Lewis et al., *Nature* (1995) 377:432-35; and G. Burnstock, *Neurophamacol.* (1997) 36:1127-39). The structure and chromosomal mapping of mouse genomic P2X$_3$ receptor subunit has also been described (V. Souslova et al., *Gene* (1997) 195:101-11). In vitro, co-expression of P2X$_2$ and P2X$_3$ receptor subunits is necessary to produce ATP-gated currents with the properties seen in some sensory neurons (C. Lewis et al., supra).

P2X receptor subunits are found on afferents in rodent and human bladder urothelium. Data exists suggesting that ATP may be released from epithelial/endothelial cells of the urinary bladder or other hollow organs as a result of distention (G. Burnstock, *J. Anatomy* (1999) 194:335-42; and D. R. Ferguson et al., *J. Physiol.* (1997) 505:503-11). ATP released in this manner may serve a role in conveying information to sensory neurons located in subepithelial components, e.g., suburothelial lamina propria (S. Namasivayam et al., *BJU Intl.* (1999) 84:854-60). The P2X receptors have been studied in a number of neurons, including sensory, sympathetic, parasympathetic, mesenteric, and central neurons (Y. Zhong et al., *Br. J. Pharmacol.* (1998) 125:771-81). These studies indicate that purinergic receptors play a role in afferent neurotransmission from the bladder, and that modulators of P2X receptors are potentially useful in the treatment of bladder disorders and other genitourinary diseases or conditions.

Recent evidence also suggests a role of endogenous ATP and purinergic receptors in nociceptive responses in mice (M. Tsuda et al., *Br. J. Pharmacol.* (1999) 128:1497-504). ATP-induced activation of P2X receptors on dorsal root ganglion nerve terminals in the spinal cord has been shown to stimulate release of glutamate, a key neurotransmitter involved in nociceptive signaling (J. G. Gu and A. B. MacDermott, *Nature* (1997) 389:749-53). P2X$_3$ receptors have been identified on nociceptive neurons in the tooth pulp (S. P. Cook et al., *Nature* (1997) 387:505-08). ATP released from damaged cells may thus lead to pain by activating P2X$_3$ and/or P2X$_{2/3}$ containing receptors on nociceptive sensory nerve endings. This is consistent with the induction of pain by intradermally applied ATP in the human blister-base model (T. Bleehen, *Br J Pharmacol* (1978) 62:573-77). P2X antagonists have been shown to be analgesic in animal models (B. Driessen and K. Starke, *Naunyn Schmiedebergs Arch Pharmacol* (1994) 350:618-25). This evidence suggests that P2X$_2$ and P2X$_3$ are involved in nociception, and that modulators of P2X receptors are potentially useful as analgesics.

Other researchers have shown that P2X$_3$ receptors are expressed in human colon, and are expressed at higher levels in inflamed colon than in normal colon (Y. Yiangou et al, *Neurogastroenterol Mot* (2001) 13:365-69). Other researchers have implicated the P2X$_3$ receptor in detection of distension or intraluminal pressure in the intestine, and initiation of reflex contractions (X. Bian et al., *J Physiol* (2003) 551.1: 309-22), and have linked this to colitis (G. Wynn et al., *Am J Physiol Gastrointest Liver Physiol* (2004) 287:G647-57).

Inge Brouns et al. (*Am J Respir Cell Mol Biol* (2000) 23:52-61) found that P2X$_3$ receptors are expressed in pulmonary neuroepithelial bodies (NEBs), implicating the receptor in pain transmission in the lung. More recently, others have implicated P2X$_2$ and P2X$_3$ receptors in pO$_2$ detection in pulmonary NEBs (W. Rong et al., *J Neurosci* (2003) 23(36): 11315-21).

There is accordingly a need for methods of treating diseases, conditions and disorders mediated by P2X$_3$ receptors, as well as a need for compounds that act as modulators of P2X receptors, including antagonists of P2X$_3$ receptors. The present invention satisfies these needs as well as others.

SUMMARY OF THE INVENTION

The invention provides methods for treating a disease mediated by a P2X$_3$ receptor antagonist, said method comprising administering to a subject in need thereof an effective amount of a compound of formula (I):

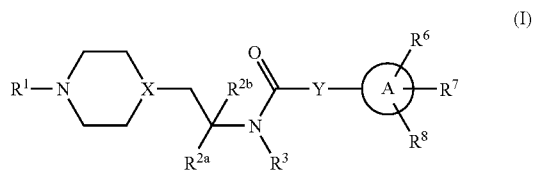

wherein R$^1$ is —C(=S)CH$_3$, pyridyl, pyrimidinyl, pyrazinyl, thiazolyl, furyl, furylcarbonyl, acetyl, or carbamoyl;
R$^{2a}$ and R$^{2b}$ are independently H, methyl, or ethyl;
R$^3$ is H or methyl;
Y is a bond, —(CR$^4$R$^5$)$_n$— or —CR$^4$=CR$^5$—; wherein R$^4$ and R$^5$ are each independently H or methyl and n is 1 or 2;
X is N or CH;

A is phenyl, 5-membered heterocyclyl, or 6-membered heterocyclyl;

$R^6$, $R^7$ and $R^8$ are each independently H, halo, lower alkyl, cycloalkyl, alkylthio, alkylthio-lower alkyl, alkylsulfonyl-lower alkyl, di(lower alkyl)amino-lower alkyl, morpholinyl-lower alkyl, 4-methyl-piperazinyl-methyl, trifluoromethyl, pyridyl, tetrazolyl, thiophenyl, phenyl, biphenyl, or benzyl; where thiophenyl, phenyl and benzyl are substituted with 0-3 lower alkyl, halo, sulfonamido, trifluoromethyl, lower alkoxy or lower alkylthio; or $R^6$ and $R^7$ together form a 5-membered or 6-membered carbocyclic or heterocyclic ring substituted with 0-3 substituents selected from the group consisting of lower alkyl, lower alkoxy, oxo, halo, thiophenyl-lower alkyl, phenyl, benzyl; where phenyl and benzyl are substituted with 0-3 lower alkyl, halo, sulfonamido, trifluoromethyl, lower alkoxy, lower alkylthio, amino-lower alkyl, lower alkylamino-lower alkyl, or di(lower alkyl)amino-lower alkyl; and pharmaceutically acceptable salts thereof;

wherein when $R^1$ is pyrimidin-2-yl, X is N, Y is a bond and A is oxazol-5-yl the carbon atom at position 4 in said oxazol-5-yl is not substituted by propyl when the carbon atom at position 2 in said oxazol-5-yl is substituted by substituted phenyl and the carbon atom at position 4 in said oxazol-5-yl is not substituted by phenyl when the carbon atom at position 2 is substituted by unsubstituted or substituted phenyl.

Another aspect of the invention is a method for modulating the activity of a $P2X_3$ receptor, comprising contacting a P2X3 receptor with a compound of formula I.

Another aspect of the invention is a method for treating genitourinary disorders responsive to $P2X_3$ modulators, comprising administering to a subject in need thereof a compound of formula 1.

Another aspect of the invention is a formulation for treating genitourinary disorders responsive to $P2X_3$ modulators, comprising administering to a subject in need thereof a compound of formula 1.

Another aspect of the invention is a method for treating gastrointestinal disorders responsive to $P2X_3$ modulators, comprising administering to a subject in need thereof a compound of formula 1.

Another aspect of the invention is a formulation for treating gastrointestinal disorders responsive to $P2X_3$ modulators, comprising administering to a subject in need thereof a compound of formula 1.

Another aspect of the invention is a method for treating respiratory disorders responsive to P2X3 modulators, comprising administering to a subject in need thereof a compound of formula 1.

Another aspect of the invention is a formulation for treating respiratory disorders responsive to $P2X_3$ modulators, comprising administering to a subject in need thereof a compound of formula 1.

Another aspect of the invention is a method for treating pain responsive to P2X3 modulators, comprising administering to a subject in need thereof a compound of formula 1.

Another aspect of the invention is a formulation for treating pain symptoms responsive to $P2X_3$ modulators, comprising administering to a subject in need thereof a compound of formula 1.

DETAILED DESCRIPTION OF THE INVENTION

All publications cited in this disclosure are incorporated herein by reference in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$ alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —R'—R", where R' is oxo and R" is alkyl as defined herein.

"Alkylsulfonyl" means a moiety of the formula —R'—R", where R' is —$SO_2$— and R" is alkyl as defined herein.

"Alkylsulfonylalkyl means a moiety of the formula —R'—R"—R'" where R' is alkyl, R" is —$SO_2$— and R'" is alkyl as defined herein.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylalkyl" and "Aralkyl", which may be used interchangeably, mean a radical-$R^a R^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Cyanoalkyl" "means a moiety of the formula —R'—R", where R' is alkylene as defined herein and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkyl-amino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" means a moiety of the formula —R'—R", where R' is alkylene and R" is cycloalkyl as defined herein.

"Heteroalkyl" means an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent moiety consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homo-piperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydroisoquinolinyl, tetrahydroquinolinyl, tetrahydroisoquinolinyl, and the like.

"Hydroxyalkyl" means an alkyl moiety as defined herein, substituted with one or more, preferably one, two or three hydroxy groups, provided that the same carbon atom does not carry more than one hydroxy group. Representative examples include, without limitation, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, without limitation, 2-, 3-, or 4-hydroxycyclohexyl, and the like.

"Urea" or "ureido" means a group of the formula —NR'—C(O)—NR"R"' wherein R', R" and R"' are each independently hydrogen or alkyl.

"Carbamate" means a group of the formula —O—C(O)—NR'R" wherein R' and R" are each independently hydrogen or alkyl.

"Carboxy" means a group of the formula —O—C(O)—OH.

"Sulfonamido" means a group of the formula —$SO_2$—NR'R" wherein R', R" and R"' each independently is hydrogen or alkyl.

"Optionally substituted", when used in association with "aryl", "phenyl", "heteroaryl" "cyclohexyl" or "heterocyclyl", means an aryl, phenyl, heteroaryl, cyclohexyl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —$(CR'R")_n$—COOR (where n is an integer from 0 to 5, R' and R" are independently hydrogen or alkyl, and R is hydrogen, alkyl, cycloalkyl, cycloalkylalkyl, phenyl or phenylalkyl), or —$(CR'R")_{n-CONR}{}^aR^b$ (where n is an integer from 0 to 5, R' and R" are independently hydrogen or alkyl, and $R^a$ and $R^b$ are, independently of each other, hydrogen, alkyl, cycloalkyl, cycloalkylalkyl, phenyl or phenylalkyl).

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulfuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Genitourinary disorders" and "disorders of the urinary tract" or "uropathy" used interchangeably with "symptoms of the urinary tract" mean the pathologic changes in the genitourinary tract. Examples of urinary tract disorders include, but are not limited to, incontinence, benign prostatic hypertrophy (BPH), prostatitis, detrusor hyperreflexia, outlet obstruction, urinary frequency, nocturia, urinary urgency, overactive bladder, pelvic hypersensitivity, urge incontinence, urethritis, prostatodynia, cystitis, idiophatic bladder hypersensitivity, and the like.

"Disease states associated with the urinary tract" or "urinary tract disease states" or "uropathy" used interchangeably with "symptoms of the urinary tract" mean the pathologic changes in the urinary tract, or dysfunction of urinary bladder smooth muscle or its innervation causing disordered urinary storage or voiding. Symptoms of the urinary tract include, but are not limited to, overactive bladder (also known as detrusor hyperactivity), outlet obstruction, outlet insufficiency, and pelvic hypersensitivity.

"Overactive bladder" or "detrusor hyperactivity" includes, but is not limited to, the changes symptomatically manifested as urgency, frequency, altered bladder capacity, incontinence, micturition threshold, unstable bladder contractions, sphincteric spasticity, detrusor hyperreflexia (neurogenic bladder), detrusor instability, and the like.

"Outlet obstruction" includes, but is not limited to, benign prostatic hypertrophy (BPH), urethral stricture disease, tumors, low flow rates, difficulty in initiating urination, urgency, suprapubic pain, and the like.

"Outlet insufficiency" includes, but is not limited to, urethral hypermobility, intrinsic sphincteric deficiency, mixed incontinence, stress incontinence, and the like.

"Pelvic Hypersensitivity" includes, but is not limited to, pelvic pain, interstitial (cell) cystitis, prostatodynia, prostatitis, vulvadynia, urethritis, orchidalgia, overactive bladder, and the like.

"Gastrointestinal disorder" refers to, without limitation, inflammatory disorders of the bowel, colon, and/or rectum, including irritable bowel syndrome (IBS), inflammatory bowel disease (IBD), Crohn's disease, ulcerative colitis, and the like.

"Respiratory disorder" refers to, without limitation, chronic obstructive pulmonary disease (COPD), asthma, bronchospasm, and the like.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any. "Treating" or "treatment" of a disease state includes:

(i) preventing the disease state, i.e. causing the clinical symptoms of the disease state not to develop in a subject that may be exposed to or predisposed to the disease state, but does not yet experience or display symptoms of the disease state.

(ii) inhibiting the disease state, i.e., arresting the development of the disease state or its clinical symptoms, or (iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom. For example, oxazol-5-yl can be illustrated by the following structure

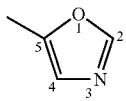

All patents and publications identified herein are incorporated herein by reference in their entirety.

General Method

The invention provides compounds of formula I that are useful modulators of $P2X_3$ receptor activity:

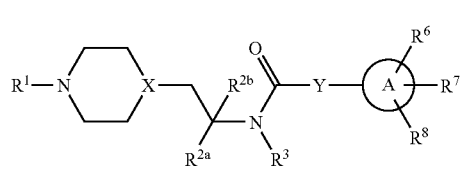

(I)

wherein $R^1$ is —C(=S)CH$_3$, pyridyl, pyrimidinyl, pyrazinyl, thiazolyl, furyl, furylcarbonyl, acetyl, or carbamoyl;

$R^{2a}$ and $R^{2b}$ are independently H, methyl, or ethyl;

$R^3$ is H or methyl;

Y is a bond, —(CR$^4$R$^5$)$_n$— or —CR$^4$=CR$^5$—; wherein $R^4$ and $R^5$ are each independently H or methyl and n is 1 or 2;

X is N or CH;

A is phenyl, 5-membered heterocyclyl, or 6-membered heterocyclyl;

$R^6$, $R^7$ and $R^8$ are each independently H, halo, lower alkyl, cycloalkyl, alkylthio, alkylthio-lower alkyl, alkylsulfonyl-lower alkyl, di(lower alkyl)amino-lower alkyl, morpholinyl-lower alkyl, 4-methyl-piperazinyl-methyl, trifluoromethyl, pyridyl, tetrazolyl, thiophenyl, phenyl, biphenyl, or benzyl; where thiophenyl, phenyl and benzyl are substituted with 0-3 lower alkyl, halo, sulfonamido, trifluoromethyl, lower alkoxy or lower alkylthio; or $R^6$ and $R^7$ together form a 5-membered or 6-membered carbocyclic or heterocyclic ring substituted with 0-3 substituents selected from the group consisting of lower alkyl, lower alkoxy, oxo, halo, thiophenyl-lower alkyl, phenyl, benzyl; where phenyl and benzyl are substituted with 0-3 lower alkyl, halo, sulfonamido, trifluoromethyl, lower alkoxy, lower alkylthio, amino-lower alkyl, lower alkylamino-lower alkyl, or di(lower alkyl)amino-lower alkyl;

and pharmaceutically acceptable salts thereof;

wherein when $R^1$ is pyrimidin-2-yl, X is N, Y is a bond and A is oxazol-5-yl the carbon atom at position 4 in said oxazol-5-yl is not substituted by propyl when the carbon atom at position 2 in said oxazol-5-yl is substituted by substituted phenyl and the carbon atom at position 4 in said oxazol-5-yl is not substituted by phenyl when the carbon atom at position 2 is substituted by unsubstituted or substituted phenyl.

In a presently preferred class of the invention, $R^{2a}$ is methyl, $R^{2b}$ and $R^3$ are H, and Y is a bond. A particularly preferred subclass of the invention is that wherein A is oxazolyl, thiazolyl, or furanyl, particularly where $R^6$, $R^7$, and $R^8$ are each independently selected from the group consisting of methyl, propyl, t-butyl, phenyl, fluorophenyl, chlorophenyl, methylthioethyl, methylsulfanylethyl, morpholino-methyl, 4-methyl-piperazin-1-ylmethyl, trifluoromethyl, benzyl, halo-benzyl, and methoxyphenyl. Presently preferred embodiments of this group are those wherein $R^1$ is pyrimidinyl, amino-pyrimidinyl, acetyl, thioacetyl, or thiazolyl.

Another presently-preferred subclass of the invention is that wherein A is pyrazolyl, triazolyl, or pyrrolyl, particularly where $R^6$, $R^7$, and $R^8$ are each independently selected from the group consisting of methyl, propyl, t-butyl, phenyl, fluorophenyl, chlorophenyl, methylphenyl, biphenyl, isopropyl, pyridyl, methoxyphenyl, methylthiophenyl, trifluoromethylphenyl, or morpholino-propyl. Presently preferred embodiments of this group are those wherein $R^1$ is pyrimidinyl or acetyl.

Another presently-preferred subclass of the invention is that wherein A is 1H-thieno-[2,3-c]pyrazolyl, indolyl, indazolyl, pyrazolyl[1,5-a]pyrimidinyl, 6,7-dihydro-5H-pyrazolo[1,5-a]pyrazin-4-onyl, 2H-phthalazin-1-onyl, or imidazo[1,5-a]pyridinyl, particularly where $R^6$, $R^7$, and $R^8$ are each independently selected from the group consisting of methyl, ethyl, cyclopropyl, s-butyl, n-butyl, cyclopentyl, phenyl, fluorophenyl, alkylphenyl, benzyl, halobenzyl, trifluoromethyl, methoxybenzyl, thiophenylmethyl, trifluoromethylphenyl, or pyridyl. Presently preferred embodiments of this group are those wherein $R^1$ is pyrimidinyl or acetyl.

Another presently preferred subclass of the invention is that wherein A is benzofuranyl, dihydrobenzofuranyl, pyridyl, pyrimidinyl, or phenyl, particularly where $R^6$, $R^7$, and $R^8$ are each independently selected from the group consisting of methyl, methoxy, phenyl, methoxyphenyl, halo, alkylphenyl, thiophenyl, methylthiophenyl, halophenyl, tetrazolyl, and propyl. Presently preferred embodiments of this group are those wherein $R^1$ is pyrimidinyl or acetyl.

Another presently preferred subclass of the invention is that wherein $R^1$ is —C(=S)CH$_3$, pyridyl, pyrimidinyl, pyrazinyl, thiazolyl, furylcarbonyl, acetyl or carbamoyl wherein when $R^1$ is pyrimidin-2-yl, X is N, Y is a bond and A is oxazol-5-yl the carbon atom at position 4 in said oxazol-5-yl is not substituted by propyl when the carbon atom at position 2 in said oxazol-5-yl is substituted by substituted phenyl and the carbon atom at position 4 in said oxazol-5-yl is not substituted by phenyl when the carbon atom at position 2 is substituted by unsubstituted or substituted phenyl.

Another presently preferred subclass of the invention is that wherein $R^{2a}$ is methyl and $R^{2b}$ is H; or $R^{2a}$ and $R^{2b}$ are methyl.

Another presently preferred subclass of the invention is that wherein $R^3$ is H.

Another presently preferred subclass of the invention is that wherein Y is a bond wherein when $R^1$ is pyrimidin-2-yl, X is N and A is oxazol-5-yl the carbon atom at position 4 in said oxazol-5-yl is not substituted by propyl when the carbon atom at position 2 in said oxazol-5-yl is substituted by substituted phenyl and the carbon atom at position 4 in said oxazol-5-yl is not substituted by phenyl when the carbon atom at position 2 is substituted by unsubstituted or substituted phenyl. Another presently preferred subclass of the invention is that wherein Y is —(CR$^4$R$^5$)$_n$— or —CR$^4$=CR$^5$—; wherein $R^4$ and $R^5$ are each independently H or methyl and n is 1 or 2. Still another presently preferred subclass of the invention is that wherein Y is —CH$_2$—, —CH$_2$CH$_2$— or —CH=CH—.

Another presently preferred subclass of the invention is that wherein A is phenyl, oxazolyl, thiazolyl, furanyl, pyrimidinyl, pyridinyl, pyrazolyl, imidazolyl, pyrrolyl, 1H-[1,2,3]triazolyl or 4,5-dihydro-1H-[1,2,4]triazolyl, wherein when A is oxazol-5-yl, $R^1$ is pyrimidin-2-yl, X is N and Y is a bond the carbon atom at position 4 in said oxazol-5-yl is not substituted by propyl when the carbon atom at position 2 in said oxazol-5-yl is substituted by substituted phenyl and the carbon atom at position 4 in said oxazol-5-yl is not substituted by phenyl when the carbon atom at position 2 is substituted by unsubstituted or substituted phenyl. Still another presently preferred subclass of the invention is that wherein A is

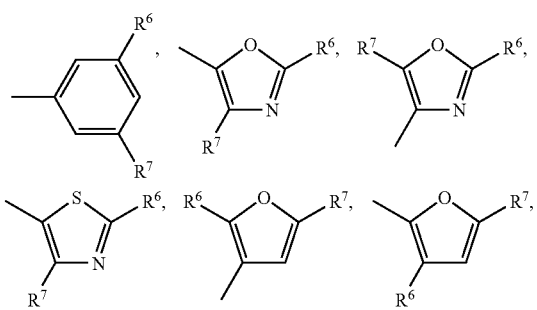

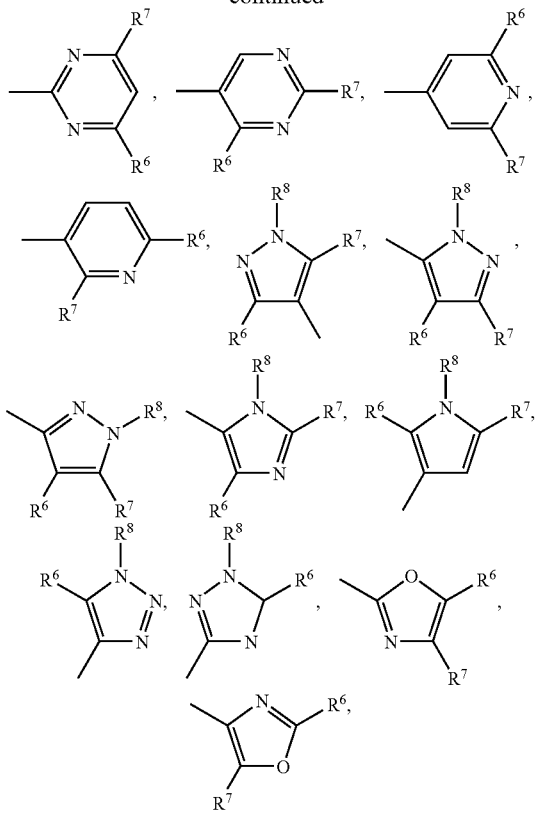

wherein $R^6$, $R^7$ and $R^8$ are each independently H, halo, lower alkyl, cycloalkyl, alkylthio, alkylthio-lower alkyl, alkylsulfonyl-lower alkyl, di(lower alkyl)amino-lower alkyl, morpholinyl-lower alkyl, 4-methyl-piperazinyl-methyl, trifluoromethyl, pyridyl, tetrazolyl, thiophenyl, phenyl, biphenyl, or benzyl;

where thiophenyl, phenyl and benzyl are substituted with 0-3 lower alkyl, halo, sulfonamido, trifluoromethyl, lower alkoxy or lower alkylthio, wherein when A is oxazol-5-yl, $R^1$ is pyrimidin-2-yl, X is N and Y is a bond the carbon atom at position 4 in said oxazol-5-yl is not substituted by propyl when the carbon atom at position 2 in said oxazol-5-yl is substituted by substituted phenyl and the carbon atom at position 4 in said oxazol-5-yl is not substituted by phenyl when the carbon atom at position 2 is substituted by unsubstituted or substituted phenyl.

Still another presently preferred subclass of the invention is that wherein $A(R^6)(R^7)R^8$ is pyrazolo[1,5a]pyrimidinyl, 1H-thieno[2,3-c]pyrazolyl, 1H-indazolyl, 2H-indazolyl, 1H-indolyl, benzofuranyl, 2H-phthalazinyl, imidazo[1,5-a]pyridyl or 4,5,6,7-tetrahydropyrazolo[1,5-a]-pyrazinyl each of which substituted with 0-3 substituents selected from the group consisting of lower alkyl, lower alkoxy, oxo, halo, thiophenyl-lower alkyl, phenyl, benzyl; where phenyl and benzyl are substituted with 0-3 lower alkyl, halo, sulfonamido, trifluoromethyl, lower alkoxy, lower alkylthio, amino-lower alkyl, lower alkylamino-lower alkyl, or di(lower alkyl)amino-lower alkyl.

Still another presently preferred subclass of the invention is that wherein —A(R$^6$)(R$^7$)R$^8$ is

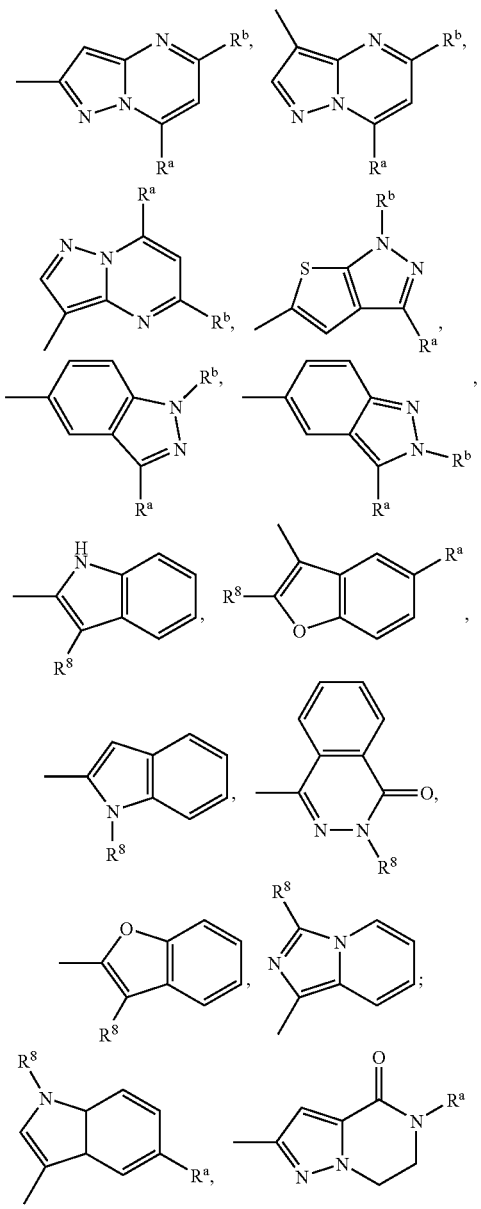

wherein $R^a$, $R^b$ band $R^8$ are each independently hydrogen; halogen; alkyl; alkyl substituted by 1 to 3 halogen; phenyl; phenyl substituted by halogen, alkyl or haloalkyl; cycloalkyl; alkoxy; benzyl; benzyl substituted by halogen; pyridinyl; or thiophenyl substituted by alkyl.

Compounds of the invention can be prepared by a variety of different synthetic schemes. For example, Scheme I illustrates a general synthesis of compounds of the invention. In Scheme I, $R^1$, $X^1$, and Ar are as defined above. "G" represents a protecting group, for example t-butyl. The carbon atom that $R^1$ is attached to can be racemic or chiral. In step I.a, a substituted piperazine is condensed with an equimolar amount of a protected alpha-aminoaldehyde, for example using excess $HB(OAc)_3$ in an aprotic solvent such as dichloroethane at room temperature until the reaction is complete. The protecting group is then removed by means appropriate to the group selected; for example, t-butyl can be removed by hydrolysis with trifluoroacetic acid (TFA). In step I.b, the deprotected intermediate is condensed with a carboxylic acid (Ar—COOH) or equivalent under basic catalysis to form the product. The product can then be purified, e.g., by extraction, crystallization, preparative HPLC, and the like.

SCHEME I:

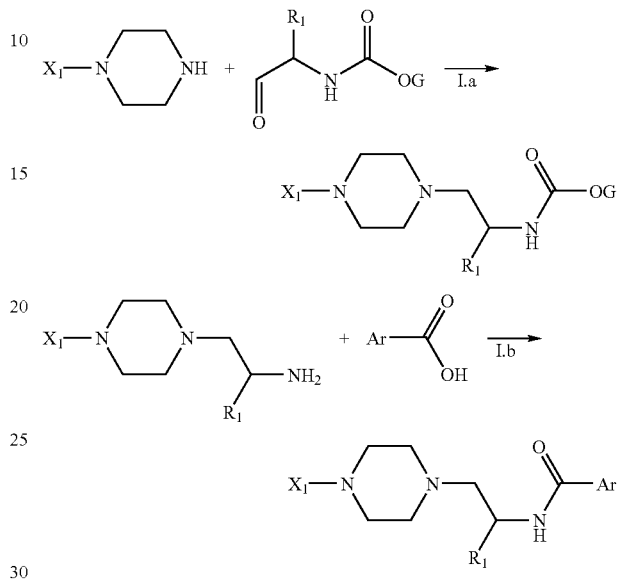

For example, Scheme II illustrates a general synthesis of compounds of the invention. In Scheme I, $R^1$, $X^1$, and Ar are as defined above. "$G^1$" and $G^2$ represents a protecting groups, for example t-butyl and where $G^1$ cannot equal $G^2$. LG is a leaving group. The carbon atom that $R^1$ is attached to can be racemic or chiral. In step II.a, an orthogonally protected piperazine is condensed with an equimolar amount of a protected alpha-aminoaldehyde, for example using excess $HB(OAc)_3$ in an aprotic solvent such as dichloroethane at room temperature until the reaction is complete. The first protecting group, G2, is then removed by means appropriate to the group selected; for example, t-butyl can be removed by hydrolysis with trifluoroacetic acid (TFA). In step II.b, the mono-deprotected intermediate is condensed with a carboxylic acid (Ar—COOH) or equivalent under basic catalysis to form the product. The product can then be purified, e.g., by extraction, crystallization, preparative HPLC, and the like. The remaining protecting group, a carbobenzyloxy group, is removed by hydrogen and palladium on carbon. In step II.c, the deprotected intermediate is reacted with an acid chloride, sulfonyl chloride, carbamoyl chloride, isocyanate, chloroformate or other derivatizing agent to form the product. The product can then be purified, e.g., by extraction, crystallization, preparative HPLC, and the like.

SCHEME II:

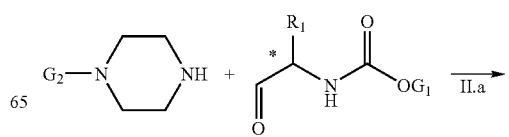

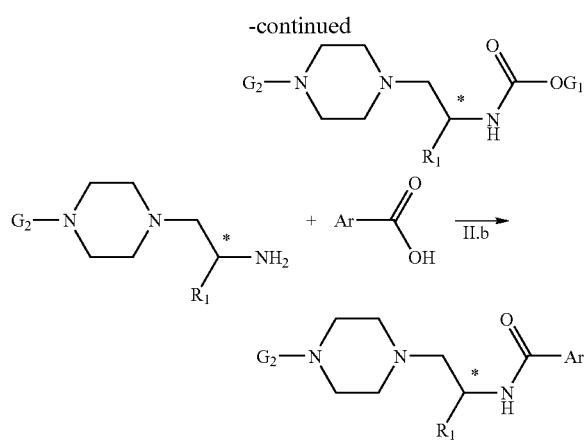

Representative compounds of the invention are set forth in the Examples below.

Specific screening methods are known in the art and along with integrated robotic systems and collections of chemical compounds/natural products are extensively incorporated in high throughput screening so that large numbers of test compounds can be tested for antagonist or agonist activity within a short amount of time. These methods include homogeneous assay formats such as fluorescence resonance energy transfer, fluorescence polarization, time-resolved fluorescence resonance energy transfer, scintillation proximity assays, reporter gene assays, fluorescence quenched enzyme substrate, chromogenic enzyme substrate and electrochemilumin-escence, as well as more traditional heterogeneous assay formats such as enzyme-linked immunosorbant assays (ELISA) or radio-immunoassays. Homogeneous assays are preferred. Also comprehended herein are cell-based assays, for example those utilizing reporter genes, as well as functional assays that analyze the effect of an antagonist or agonist on biological function(s) or activity(ies) of compounds of the invention on $P2X_3$ receptors, and biological systems containing P2X3 receptors.

Compositions comprising an effective amount of a compound of the present invention, in combination with other components such as a physiologically acceptable diluent, carrier, or excipient, are provided herein. The compounds can be formulated according to known methods used to prepare pharmaceutically useful compositions. They can be combined in admixture, either as the sole active material or with other known active materials suitable for a given indication, with pharmaceutically acceptable diluents (for example, saline, Tris-HCl, acetate, and phosphate buffered solutions), preservatives (for example, thimerosal, benzyl alcohol, parabens), emulsifiers, solubilizers, adjuvants and/or carriers. Suitable formulations for pharmaceutical compositions include those described in "Remington's Pharmaceutical Sciences", 16th ed. 1980, Mack Publishing Company, Easton, Pa.

In addition, such compositions can be complexed with polyethylene glycol (PEG), metal ions, or incorporated into polymeric compounds such as polyacetic acid, polyglycolic acid, hydrogels, dextran, and the like, or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance, and are thus chosen according to the intended application.

The compositions of the invention can be administered in any suitable manner, e.g., topically, parenterally, or by inhalation. The term "parenteral" includes injection, e.g., by subcutaneous, intravenous, or intramuscular routes, also including localized administration, e.g., at a site of disease or injury. Those of ordinary skill in the art recognize that other types of localized administration (e.g., intraarticular, intracapsular, intracarpal, intracelial, intracerebro-ventricular, intrasynovial, intraspinal, intraligamentus, intrameningeal, intraocular, epidural, transepithelially, and/or administration by one or more of these routes at a site near or adjacent to a site of disease or injury) are suitable for use in administering the compositions of the present invention. Sustained release from implants is also contemplated.

One skilled in the pertinent art will recognize that suitable dosages will vary, depending upon such factors as the nature of the disorder to be treated, the patient's body weight, age, and general condition, and the route of administration. Preliminary doses can be determined according to animal tests, and the scaling of dosages for human administration is performed according to art-accepted practices.

Utility

Compounds of the invention are useful for treating a wide range of genitourinary diseases, conditions and disorders, including urinary tract disease states associated with bladder outlet obstruction and urinary incontinence conditions such as reduced bladder capacity, frequency of micturition, urge incontinence, stress incontinence, bladder hyperreactivity, benign prostatic hypertrophy (BPH), prostatitis, detrusor hyperreflexia, urinary frequency, nocturia, urinary urgency, overactive bladder, pelvic hyper-sensitivity, urethritis, pelvic pain syndrome, prostatodynia, cystitis, and idiopathic bladder hypersensitivity, and other symptoms related to overactive bladder. Compounds of the invention are also useful for treating gastrointestinal disorders, including inflammatory bowel syndrome (IBS), inflammatory bowel disease (IBD), reduced diarrhea in D-dominant IBS, and the like. Further, compounds of the invention are useful for treating respiratory disorders, including chronic obstructive pulmonary disorder (COPD), asthma, bronchospasm, and the like.

The compounds of the invention are useful as analgesics in the treatment of diseases and conditions associated with pain from a wide variety of causes, including, but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

EXAMPLES

The following preparations and examples are given to enable those skilled in the art to more clearly understand and to practice the present invention. They should not be considered as limiting the scope of the invention, but merely as being illustrative and representative thereof.

Example 1

Preparation of 2-(4-fluorophenyl)-4-propyl-oxazole-5-carboxylic acid {2-[4-(6-aminopyridin-2-yl)-piperazin-1-yl]-1-methyl-ethyl}amide (A) To a solution of 6-chloro-2-pyridinylamine (406 mg, 3.16 mmol) and piperazine (381 mg, 4.42 mmol) in m-xylene (10 ml), were added sodium tert-butoxide (425 mg, 4.42 mmol) and bis-(tri-o-tolylphosphine)palladium(II) dichloride (124 mg, 0.158 mmol). The mixture was heated at reflux under $N_2$ for 24 h. The reaction was cooled down and tetrahydrofuran (THF, 10 ml) added, and the mixture was filtered on a celite pad. The filtrate was evaporated and purified via flash chromatography ($CH_2Cl_2$/MeOH/$NH_4OH$) affording 30 mg of 2-amino-6-(piperazin-1-yl)pyridine (intermediate "Ia") as a tan solid (5% yield). H-NMR ($CD_3OD$): 2.95 (m, 4H), 3.47 (m, 4H), 5.93 (m, 1H), 6.01 (m, 1H), 7.24 (m, 1H). $M^+$=179.

(B) To a solution of intermediate Ia (30 mg, 0.169 mmol) in dichloroethane (DCE, 10 mL) was added (1-methyl-2-oxoethyl)-carbamic acid t-butyl ester (29 mg, 0.169 mmol) and sodium triacetoxyborohydride ($NaBH(OAc)_3$, 71 mg, 0.339 mmol). The reaction mixture was stirred at room temperature (RT) for 60 h. The solvent was evaporated, and the residue was partitioned between $CH_2Cl_2$ and a saturated solution of $NaHCO_3$, the organic layer was separated and washed twice with a saturated solution of $NaHCO_3$ to provide {2-[4-(6-aminopyridin-2-yl)-piperazin-1-yl]-1-methyl-ethyl}-carbamic acid t-butyl ester (intermediate Ib). The crude mixture was used without further purification for the deprotection reaction. $M^+$=336.

(C) The crude mixture from part (B) above was dissolved in $CH_2Cl_2$ (1.5 ml) and TFA (0.5 ml) was added at 0° C. The mixture was stirred at 0° C. for 5 min., then at RT for 4 h to provide the deprotected product, 6-[4-(2-aminopropyl)-piperazin-1-yl]-pyridin-2-ylamine (intermediate Ic). The solvent was evaporated and the crude mixture used without further purification. $M^+$=236.

(D) 3-oxo-hexanoic acid ethyl ester (29.7 g, 188 mmol) was dissolved in $Et_2O$ (400 ml). The solution was cooled to 0° C., and sulfuryl chloride (22.6 ml, 282 mmol) was added dropwise. The solution gradually warmed to RT over 4 h. The solution was neutralized to pH 7 with a solution of aqueous saturated $NaHCO_3$. The organic layer was separated, washed with brine, and dried over sodium sulfate. Evaporation under reduced pressure yielded 2-chloro-3-oxo-hexanoic acid ethyl ester (intermediate Id, 36 g, 100%). $^1$H-NMR ($CDCl_3$, ppm): 0.95 d (3H); 1.35 d (3H); 1.58 m (2H); 2.7 t (2H); 4.28(d (2H); 4.78 s (1H).

(E) Intermediate Id (36 g, 188 mmol) was combined with 4-fluorobenzamide (26.2 g, 188 mmol), and the reaction mixture heated to 150° C. for 4 h. The residue was purified by flash chromatography on silica gel with gradient elution (0% to 2% EtOAc in hexanes) to provide 2-(4-fluorophenyl)-4-propyl-oxazole-5-carboxylic acid ethyl ester (intermediate Ie, 3.18 g, 6.1%). $^1$H-NMR ($CDCl_3$, ppm) 1.0 t (3H); 1.42 t (3H); 1.77 m (2H); 2.88 t (2H); 4.4 q (2H); 7.17 t (2H); 8.14 t (2H).

(F) Intermediate Ie (3.18 g, 11.5 mmol) was dissolved in THF (80 ml) and water (8 ml), and 15% aqueous NaOH (15 ml) was added. The reaction mixture was heated to 70° C. for 3 h, then cooled to RT. The organic solvents were removed by evaporation under reduced pressure, and the residue taken up in water (100 ml). HCl (6 N) was added to adjust the pH of the solution to 1. The resulting solid was filtered and dried under reduced pressure to yield 2-(4-fluoro-phenyl)-4-propyl-oxazole-5-carboxylic acid (intermediate If, 3 g, 100%). $^1$H-NMR ($CDCl_3$, ppm): 1.05 t (3H); 1.70 sextet (2H); 2.93 t (2H); 7.17 t (2H); 8.17 t (2H).

(G) To a suspension of dicyclohexylcarbodiimide polymer supported (250 mg, 0.338 mmol) in $CH_2Cl_2$ (3 ml) were added 2-(4-fluorophenyl)-4-propyl-oxazole-5-carboxylic acid (46 mg, 0.186 mmol), intermediate "If", and hydroxybenzotriazole (HOBT, 34 mg, 0.253 mmol). The mixture was stirred at RT for 2 h, then the crude intermediate Ic in $CH_2Cl_2$ solution (2 ml) and diisopropylethylamine (0.147 ml, 0.845 mmol) was added. The mixture was stirred for 20 h at RT. The resin was filtered off and washed with dichloromethane. The filtrate was washed with a saturated solution of $NaHCO_3$, dried on sodium sulfate and evaporated. The product, 2-(4-fluorophenyl-4-propyl-oxazole-5-carboxylic acid {2-[4-(6-aminopyridin-2-yl)-piperazin-1-yl]-1-methyl-ethyl}amide (compound 1) was purified via preparative HPLC. $M^+$=467.

(H) Similarly, following the procedure set forth in Example 1(B-G) substituting 1-pyridin-2-yl-piperazine for (intermediate "Ia"), 2-(4-fluorophenyl)-4-propyl-oxazole-5-carboxylic acid [1-methyl-2-(4-pyridin-2-yl-piperazin-1-yl)-ethyl]-amide (compound 24) was prepared.

Example 2

Preparation of 2-(4-fluorophenyl)-4-propyl-oxazole-5-carboxylic acid {2-[4-(4-aminopyrimidin-2-yl)-piperazin-1-yl]-1-methyl-ethyl}amide (A) To a solution of 2,4-dichloropyrimidine (7.5 g, 50 mmol) in ethanol (EtOH, 25 ml) was added ammonium hydroxide (25 ml, 30%). The reaction mixture was stirred at RT for 18 h. The white precipitate that formed was filtered and washed with ethanol, and dried under vacuum to provide a mixture of 2-chloro-pyrimidin-4-ylamine (IIa) and 4-chloropyrimidin-2-ylamine (4.13 g, 64 % yield). (See G. Caravatti et al., *Bioorg Med Chem Lett* (1999) 9:1973-78.) $M^+$=130.

(B) To a solution of the mixture of pyrimidines (4.13 g, 32 mmol) in absolute EtOH (80 ml) were added piperazine 1-carboxylic acid benzyl ester (7.05 g, 32 mmol) and $NaHCO_3$ (8.07 g, 94 mmol). The reaction was heated at reflux for 20 h. The mixture was then cooled down, and the white precipitate of unreacted starting material was filtered off. The filtrate was evaporated and the residue was partitioned between EtOAc and water, the organic layer was separated and the aqueous phase was extracted twice with EtOAc. The organic layers were combined, dried over sodium sulfate and evaporated. The crude mixture was purified via flash chromatography ($CH_2Cl_2$/MeOH) affording 2.4 g (23% yield) of 4-(4-aminopyrimidin-2-yl)-piperazine-1-carboxylic acid benzyl ester (intermediate IIb) and 3.4 g (34% yield) of the other regioisomer. H-NMR ($CDCl_3$): 3.55 (m, 4H), 3.76 (m, 4H), 4.56 (bs, 2H), 5.17 (s, 2H), 5.78 (d, J=5.61 Hz), 7.32-7.38 (m, 5H), 7.93 (d, J=5.61 Hz).

(C) To a solution of IIb (2.4 g, 7.67 mmol) in MeOH (80 ml) at RT was added palladium 10% on carbon (600 mg). The reaction mixture was stirred under $H_2$ (approx. 2 atm) for 60 h. The catalyst was filtered on a celite pad, and the filter cake was washed with methanol. The filtrate was evaporated providing 2-piperazin-1-yl-pyrimidin-4-ylamine (intermediate IIc) (1.37 g, quantitative yield) as a white solid. H-NMR ($CD_3OD$): 2.82 (m, 4H), 3.65 (m, 5H), 5.82 (d, 1H, J=5.85), 7.72 (d, 1H, J=5.85).

(D) To a solution of IIc (985 mg, 5.5 mmol) in DCE (60 mL) were added (1-methyl-2-oxo-ethyl)-carbamic acid t-butyl ester (951 mg, 5.5 mmol) and $NaBH(OAc)_3$ (2.33 g, 11 mmol). The reaction mixture was stirred at RT for 60 h. The solvent was evaporated and the residue was partitioned between $CH_2Cl_2$ and a saturated solution of $NaHCO_3$, the organic layer was separated and washed twice with a saturated solution of $NaHCO_3$. The crude mixture was purified via flash chromatography $CH_2Cl_2$/MeOH providing {2-[4-(4-aminopyrimidin-2-yl)-piperazin-1-yl]-1-methyl-ethyl}-carbamic acid t-butyl ester (intermediate IId, 880 mg, 48% yield) as colorless oil. H-NMR ($CDCl_3$): 1.27 (d, 3H, J=11.8 Hz), 1.45 (s, 9H), 2.13-2.57 (m 7H), 3.71 (m, 5H), 4.83 (bm, 3H), 5.74 (d, 1H, J=5.64), 7.90 (d, 2H, J=5.64).

(E) Intermediate IId was deprotected following the procedure set forth in Example 1(C) above to provide 2-[4-(2-aminopropyl)-piperazin-1-yl]-pyrimidin-4-ylamine (intermediate IIe) in quantitative yield as a foamy white solid. $M^+$=237.

(F) Intermediate IIe was condensed with 2-(4-fluorophenyl)-4-propyloxazole-5-carboxylic acid as described in Example 1(G) above to provide compound 2 as a white solid in 62% yield. H-NMR (CDCl$_3$): 1.01 (t, 3H, J=7.41 Hz), 1.34 (d, 3H, J=6.39 Hz), 1.77 (m, 2H), 2.37-2.68 (m, 6H), 2.95 (m, 2H), 3.75 (m, 4H), 4.20 (m, 1H), 4.71 (bs, 2H), 5.75 (d, 1H, J=5.64 Hz), 6.80 (bd, 1H, J=6.06 Hz), 7.12 (m, 2H), 7.90 (d, 1H, J=5.61 Hz), 8.05 (m, 2H). MP=77.1-88.0° C. M$^+$=468.

Example 3

Preparation of 2-(4-fluorophenyl)-4-propyl-oxazole-5-carboxylic acid [1-methyl-2-(4-thiazol-2-ylpiperazin-1-yl)-ethyl]amide (A) Piperazine (3.44 g, 40 mmol) was added to a solution of 2-bromothiazole (1.8 ml, 20 mmol) in acetonitrile (90 ml). The mixture was heated at reflux for 20 h. The reaction was cooled down at RT and the precipitate (disubstituted piperazine) was filtered off. The filtrate was evaporated, the residue was partitioned between water and ethyl acetate, the organic phase was separated and the aqueous layer was extracted twice with EtOAc. The combined organic layers were extracted with HCl (1 M). The organic phase was discarded, and the aqueous layer was neutralized by addition of NaHCO$_3$ (solid) to pH 8, and then extracted with EtOAc. The organic extracted was dried over sodium sulfate and evaporated, providing 1-thiazol-2-ylpiperazine (intermediate IIIa, 860 mg, 25% yield) as colorless oil. H-NMR (CDCl$_3$): 2.98 (m, 4H), 3.48 (m, 4H), 6.56 (d, 1H, J=3.63 Hz), 7.20 (d, 1H, J=3.63 Hz).

(B) Proceeding as set forth in Example 2(B-C) but substituting intermediate IIIa for intermediate IIa, [1-methyl-2-(4-thiazol-2-yl-piperazin-1-yl)-ethyl]-carbamic acid t-butyl ester (intermediate IIIb) was obtained as a foamy solid in 92% yield.

(C) Intermediate IIIb was deprotected following the procedure set forth in Example 1(C) to provide 1-methyl-2-(4-thiazol-2-yl-piperazin-1-yl)-ethylamine (intermediate IIIc) in quantitative yield as a colorless oil. M$^+$=227.

(D) Following the procedure set forth in Example 1(G) above, but substituting intermediate IIIc, 2-(4-fluorophenyl)-4-propyl-oxazole-5-carboxylic acid [1-methyl-2-(4-thiazol-2-yl-piperazin-1-yl)-ethyl]-amide (compound 3) was obtained as a white solid in 75% yield. M$^+$=458.

Example 4

Preparation of 2-(4-fluorophenyl)-4-propyl-oxazole-5-carboxylic acid [1-methyl-2-(4-thioacetylpiperazin-1-yl)-ethyl]amide (A) To a solution of 1-[4-(2-amino-propyl)-piperazin-1-yl]-ethanone (149 mg, 0.4 mmol) and triethylamine (TEA, 118 µl, 0.8 mmol) was added Lawesson's reagent (162 mg, 0.4 mmol) at RT. The reaction mixture was heated at reflux for 3 h to provide 1-[4-(2-aminopropyl)-piperazin-1-yl]-ethanethione (intermediate IVa). The solvent was evaporated and the residue was partitioned between ethyl ether and HCl (1 N), the organic layer was discarded and the aqueous layer was basified by addition of a saturated solution of K$_2$CO$_3$. The aqueous solution was extracted with ethyl acetate four times. The organic layers were combined, dried over sodium sulfate and evaporated. The crude mixture was used for the next coupling reaction. M$^+$=202.

(B) Following the procedure set forth in Example 1(G) above, but substituting intermediate IVa for Ic, the compound 2-(4-fluorophenyl)-4-propyl-oxazole-5-carboxylic acid [1-methyl-2-(4-thioacetyl-piperazin-1-yl)-ethyl]-amide (compound 4) was obtained, and purified via parative HPLC to yield 15 mg of compound 4 as the TFA salt as a yellow viscous oil. M$^+$=433.

Example 6

Preparation of 2-(4-Fluorophenyl)-4-propyl-oxazole-5-carboxylic acid {(R)-2-[4-(furan-2-ylcarbonyl)-piperazin-1-yl]-1-methyl-ethyl}-amide (A) (R)-(2-hydroxy-1-methyl-ethyl)-carbamic acid tert-butyl ester (2.0 g, 11.4 mmol) in 10 mL of CH$_2$Cl$_2$ was added dropwise to a stirred solution of oxalyl chloride (1.1 mL, 12.6 mmol) and DMSO (1.62 mL, 22.8 mmole) in 20 mL of CH$_2$Cl$_2$ at −60° C. The reaction mixture was stirred for 5 minutes before TEA (5.6 ml, 57.1 mmole) was added slowly. The resultant reaction mixture was warmed to room temperature over 1 hour. The organics were washed with water, and the aqueous fractions back extracted with CH$_2$Cl$_2$. The organics were combined and dried over sodium sulfate. The solvent was evaporated under reduced pressure to provide 2.0 g (99%) of (1-methyl-2-oxo-ethyl)-carbamic acid tert-butyl ester (Intermediate VIa) ($^1$H-NMR (CDCl$_3$, ppm) 1.34 d (3H); 1.45 s (9H); 3.10 q (1H); 9.45 (1H)).

(B) 1.9 g (8.7 mmol) of piperazine-1-carboxylic acid benzyl ester was dissolved in 20 ml of 1,2-dichloroethane. 3.4 ml (34.6 mmol) of triethyl amine was added to the solution followed by 1.5 g (8.7 mmol) of Intermediate VIa and 3.7 g (17.3 mmol) sodium triacetoxyborohydride. The reaction mixture stirred for 18 hours. The solution was diluted with CH$_2$Cl$_2$ (100 ml). The organics were washed 3 times with saturated aqueous sodium bicarbonate, then dried over sodium sulfate. The solvent was evaporated under reduced pressure. The residue was purified by flash chromatography on silica gel with gradient elution (20% to 30% ethyl acetate in hexanes) to provide 2.55 g (78%) of (R)-4-(2-tert-butoxycarbonylamino-propyl)-piperazine-1-carboxylic acid benzyl ester (Intermediate VIb) (M$^+$=378).

(C) 1.51 g (4.0 mmol) of Intermediate VIb was dissolved in 50 ml of 25% trifluoroacetic acid in CH$_2$Cl$_2$. The reaction mixture stirred for 4 hours. The solvent was evaporated under reduced pressure to provide 1.6 g (99%) of (R)-4-(2-aminopropyl)-piperazine-1-carboxylic acid benzyl ester trifluoroacetic acid salt (Intermediate VI c) (M$^+$=278).

(D) 1.6 g (4.0 mmol) of Intermediate VIc was combined with 997 mg (4.0 mmol) of 2-(4-fluorophenyl)-4-propyl-oxazole-5-carboxylic acid, 805 mg (4.2 mmol) of 1-(3-dimethyl-aminopropyl)-3-ethylcarbodiimide hydrochloride, 540 mg (4.0 mmol) 1-hydroxybenzotriazole hydrate and 336 mg (16.0 mmol) sodium bicarbonate in 50 ml of dimethylformamide. The reaction mixture was stirred for 18 hours, and then filtered. The solvent was evaporated under reduced pressure, and the residue dissolved in CH$_2$Cl$_2$ (100 ml). The organics were washed with 2% hydrochloric acid followed by saturated sodium bicarbonate and brine, then dried over anhydrous sodium sulfate. The solvent was evaporated under reduced pressure, and the residue was purified by flash chromatography on silica gel (5% methanol in dichloromethane) to provide 843 mg (41%) of (R)-4-(2{[2-(4-fluoro-phenyl)-4-propyl-oxazole-5-carbonyl]-amino}-propyl)-piperazine-1-carboxylic acid benzyl ester (Intermediate VI d) (M$^+$=509).

(E) 843 mg (1.7 mmol) of Intermediate VId was dissolved in 50 ml of ethanol. 3.4 mg (0.17 mmol) of palladium on carbon (Degussa) was added. The reaction mixture stirred under atmospheric hydrogen for 18 hours. The solution was filtered through Celite™ then evaporated under reduced pressure to provide 595 mg (94%) of (R)-2-(4-fluoro-phenyl)-4-propyl-oxazole-5-carboxylic acid (1-methyl-2-pipereazin-1-yl-ethyl)-amide (Intermediate VI-e) ($M^+$=375).

134 mg (0.28 mmol) of Intermediate VI-e was dissolved in 10 ml of dichloromethane. 1.0 ml of diisopropylethyl amine was added to the reaction mixture followed by 72 mg (0.56 mmol) of 2-furoyl chloride. The reaction mixture stirred for 18 hours. The solvent was evaporated under reduced pressure. The residue was purified by flash chromatography on silica gel with gradient elution (2% to 5% methanol in dichloromethane) to provide 65.2 mg (50%) of 2-(4-fluorophenyl)-4-propyl-oxazole-5-carboxylic acid (R)-{2-[4-(furan-2-carbonyl)-piperazin-1-yl]-1-methyl-ethyl}-amide (Compound 6) ($M^+$=469).

Example 7

Preparation of 2-(4-fluorophenyl)-4-propyl-oxazole-5-carboxylic acid [(R)-1-methyl-2-(4-pyrimidin-4-yl-piperazin-1-yl)-ethyl]-amide Following the procedure set forth in Example 6A-D substituting 4-piperazin-1-yl-pyrimidine for piperazine-1-carboxylic acid benzyl ester, 2-(4-fluorophenyl)-4-propyl-oxazole-5-carboxylic acid [(R)-1-methyl-2-(4-pyrimidin-4-yl-piperazin-1-yl)-ethyl]-amide (compound 7) was prepared. $M^+$=453.

Example 8

Preparation of 2-(4-Fluorophenyl)-4-propyl-oxazole-5-carboxylic acid [(R)-1-methyl-2-(4-pyridin-2-yl-piperazin-1-yl)-ethyl]-amide (A) Following the procedure set forth in Example 6A-D substituting 1-pyridin-2-yl-piperazine for piperazine-1-carboxylic acid benzyl ester, 2-(4-fluorophenyl)-4-propyl-oxazole-5-carboxylic acid [(R)-1-methyl-2-(4-pyridin-2-yl-piperazin-1-yl)-ethyl]-amide (compound 8) was prepared as the TFA salt. $M^+$=452.

Example 9

Preparation of 2-(4-Fluorophenyl)-4-propyl-oxazole-5-carboxylic acid [(R)-1-methyl-2-(4-pyrazin-2-yl-piperazin-1-yl)-ethyl]-amide Following the procedure set forth in Example 6A-D substituting 3,4,5,6-tetrahydro-2H-[1,2']bipyrazinyl for piperazine-1-carboxylic acid benzyl ester, 2-(4-fluorophenyl)-4-propyl-oxazole-5-carboxylic acid [(R)-1-methyl-2-(4-pyrazin-2-yl-piperazin-1-yl)-ethyl]-amide (compound 9) was prepared as the TFA salt. $M^+$=453.

Example 10

Preparation of 4-((R)-2-{[2-(4-Fluorophenyl)-4-propyl-oxazole-5-carbonyl]-amino}-propyl)-piperazine-1-carboxylic acid amide Intermediate VIe (93.4 mg, 0.269 mmol) was dissolved in 0.15 ml of 17% acetic acid in water. Water (0.15 ml) was added to the solution followed by 43.6 mg (0.538 mmol) potassium cyanate. The reaction mixture stirred for 18 hours. The solvent was evaporated. Purification by reverse phase high pressure liquid chromatography gave, 4-((R)-2-{[2-(4-fluorophenyl)-4-propyl-oxazole-5-carbonyl]-amino}-propyl)-piperazine-1-carboxylic acid amide (compound 10) was prepared as the TFA salt. $M^+$=418.

Example 11

Preparation of 2-(4-Fluorophenyl)-4-propyl-oxazole-5-carboxylic acid [(R)-1-methyl-2-(4-acetyl-piperazin-1-yl)-ethyl]-amide (A) Following the procedure set forth in Example 6 but substituting acetyl chloride for 2-furoyl chloride, the compound 2-(4-fluorophenyl)-4-propyl-oxazole-5-carboxylic acid [(R)-2-(4-acetyl-piperazin-1-yl)-1-methyl-ethyl]-amide (compound 11) was prepared as a TFA salt. $M^+$=417.

Example 12

Preparation of 2-(2-Fluorophenyl)-4-(2-methylsulfanylethyl)-oxazole-5-carboxylic acid [1-methyl-2-(4-acetyl-piperazin-1-yl)-ethyl]-amide (A) To a clear solution of D,L-methionine (10 g, 67.02 mmol) and NaOH (4.0 g, 100.53 mmol) in acetone (100 ml)/$H_2O$ (100 ml) was added 2-fluorobenzoyl chloride dropwise with stirring between each addition. Basicity was maintained by adding 2N NaOH when necessary. After addition was completed, the reaction mixture was acidified to pH 2 with 6N HCl and extracted into EtOAc. The organic layer was dried with $Na_2SO_4$, filtered, and concentrated to give provide 2-(2-fluorobenzoylamino)-4-methylsulfanyl-butyric acid (intermediate XIIa, 13.6 g) as an oil.

(B) To a solution of intermediate XIIa (13 g, 47.97 mmol) in anhydrous THF (150 ml) was added oxalyl chloride (28 g, 216.1 mmol), and stirred at RT for 72 h. Solvent and excess oxalyl chloride were removed under reduced pressure. The reaction residue was cooled in an ice bath. TEA (7.3 g, 71.96 mmol) was added carefully, followed by anhydrous MeOH (200 ml). Stirring was continued for another 3 h at RT before solvent was removed under reduced pressure. The residue was flash chromatographed (silica, 20% EtOAc in hexane) yield 2-(2-fluoro-phenyl)-4-(2-methylsulfanyl-ethyl)-oxazole-5-carboxylic acid (intermediate XIIb, 11.59 g) as a cream solid.

(C) Following the procedure for XIIIc-d below substituting 1-acetylpiperazine for 2-piperazin-1-yl-pyrimidine, 1-methyl-2-(acetylpiperazin-1-yl)ethyl amine 2HCl (intermediate XIIc, 1.52 g) was prepared. $M^+$=185.

(D) To a solution of intermediate XIIb (0.2 g, 0.71 mmole) in anhydrous THF (10 mL) was added HBTU (0.27 g, 0.71 mmol), intermediate XIIc (0.27 g, 0.71 mmole) and DIEA (0.55 mL, 4.26 mmol). The reaction mixture was stirred at room temperature 18 h before concentration. Purification by flash chromatography 3% methanol in $CH_2Cl_2$ afforded compound 2-(2-fluoro-phenyl)-4-(2-methylsulfanylethyl)-oxazole-5-carboxylic acid [1-methyl-2-(4-acetylpiperazin-1-yl)-ethyl]-amide (compound 12). $M^+$=449.

Example 13

Preparation of 2-(2,4-Difluorophenyl)-4-(2-methylsulfanylethyl)-oxazole-5-carboxylic acid [1-methyl-2-(4-pyrimidin-2-yl-piperazin-1-yl)-ethyl]-amide (A) 2-t-butoxycarbonylamino-propionic acid (25 g, 132 mmole) was dissolved in dimethylformamide (DMF, 300 ml). N,O-dimethylhydroxylamine HCl (12.9 g, 132 mmol) was added, followed by 1-(3-dimethylaminopropyl)-3-ethylcarbodiimide HCl (26.6 g, 139.0 mmol), HOBT (17.8 g, 132 mmol), and NaHCO$_3$ (44.4 g, 528 mmol). The reaction mixture was stirred under nitrogen for 48 h. The solution was then filtered, and the solvent evaporated under reduced pressure. The residue was dissolved in CH$_2$Cl$_2$ and washed with 2% aqueous HCl, saturated aqueous NaHCO$_3$, and water. The organic layers were dried over sodium sulfate and evaporated under reduced pressure to provide [1-(methoxy-methyl-carbamoyl)-ethyl]-carbamic acid tert-butyl ester (intermediate XIIIa, 12.84 g, 42%). M$^+$=233.

(B) Intermediate XIIIa (12.84 g, 55.3 mmol) was dissolved in dry THF (400 ml). The solution was cooled to 0° C., and LiAlH$_4$ (69.1 ml, 69.1 mmol; 1.0 M in THF) was added dropwise. The reaction mixture stirred at 0° C. for 30 min. KHSO$_4$ (13.18 g.,) in water (200 ml) was then added dropwise, and the solution diluted with diethyl ether (500 ml). The aqueous layer was extracted 3× with diethyl ether. The organic layers were combined and washed 3× with HCl (3 N), 3× with saturated sodium bicarbonate, and twice with brine. The organic layers were dried over sodium sulfate and evaporated under reduced pressure to provide (1-methyl-2-oxo-ethyl)-carbamic acid t-butyl ester (intermediate XIIIb, 61.36 g, 69%). M$^+$=174.

(C) 2-piperazin-1-yl-pyrimidine (4.4 g, 26.6 mmol) was dissolved in DCE (125 ml), and TEA (10.5 ml, 106 mmol) added. Intermediate XIIIb (4.6 g, 26.6 mmol) was dissolved in DCE (125 ml) and added to the reaction mixture, followed by NaBH(OAc)$_3$ (11.3 g, 53 mmol). The reaction mixture was stirred 18 h, and the solution then diluted with CH$_2$Cl$_2$ and the organics were washed with saturated aqueous NaHCO3 (250 ml). The aqueous layer was back extracted with CH$_2$Cl$_2$ The combined CH$_2$Cl$_2$ extracts were dried over Na$_2$SO$_4$. The solvent was evaporated under reduced pressure, and the residue purified by flash chromatography on silica gel (5% MeOH in CH$_2$Cl$_2$) to provide [1-methyl-2-(4-pyrimidin-2-yl-piperazin-1-yl)-ethyl]-carbamic acid t-butyl ester (intermediate XIIIc, 8.5 g ) M$^+$=322.

(D) Intermediate XIIIc (8.5 g, 26 mmole) was dissolved in CH$_2$Cl$_2$ (50 mL). HCl (119 ml, 119 mmol, 1.0 M in Et$_2$O) was added. The reaction mixture was agitated for 18 hours. The solvent was evaporated under reduced pressure to yield 1-methyl-2-(4-pyrimidin-2-yl-piperazin-1-yl)ethyl amine 2HCl (intermediate XIIId, 9.34 g (100%). M$^+$=222.

(E) Following the procedure set forth in Example 12 but substituting 2,4-difluoro-benzoyl chloride for 2-fluorobenzoyl chloride, and using intermediate XIIId, the compound 2-(2,4-difluorophenyl)-4-(2-methylsulfanylethyl)-oxazole-5-carboxylic acid [1-methyl-2-(4-pyrimidin-2-yl-piperazin-1-yl)-ethyl]-amide (compound 13) was prepared.

Example 14

Preparation of 2-(2-Fluorophenyl)-4-(2-methylsulfonylethyl)-oxazole-5-carboxylic acid [1-methyl-2-(4-acetyl-piperazin-1-yl)-ethyl]-amide To a solution of compound 12 (0.16 g, 0.357 mmol) in MeOH/H$_2$O (6 ml/2 ml) was added oxone, and the mixture stirred at RT for 1 h. The reaction mixture was concentrated under reduced pressure to remove most of the MeOH. The remaining aqueous solution was extracted into CH$_2$Cl$_2$, was washed with NaOH and water; dried with K$_2$CO$_3$, filtered and concentrated. PTLC (silica, 5% MeOH/CH$_2$Cl$_2$) gave 2-(2-fluorophenyl)-4-(2-methylsulfonylethyl)-oxazole-5-carboxylic acid [1-methyl-2-(4-acetyl-piperazin-1-yl)-ethyl]-amide (compound 14, 0.1 g) as white solid. M$^+$H=481.

Example 15

Preparation of 2-(2,4-Difluorophenyl)-4-(2-methylsulfonylethyl)-oxazole-5-carboxylic acid [1-methyl-2-(4-pyrimidin-2-yl-piperazin-1-yl)-ethyl]-amide Proceeding as in Example 14 above, but substituting compound 13 for compound 12, 2-(2,4-difluorophenyl)-4-(2-methylsulfonylethyl)-oxazole-5-carboxylic acid [1-methyl-2-(4-pyrimidin-2-yl-piperazin-1-yl)-ethyl]-amide (compound 15) was prepared.

Example 16

Preparation of 2-(4-fluorophenyl)-4-propyl-oxazole-5-carboxylic acid [1-methyl-2-(4-pyrimidin-2-yl-piperidin-1-yl)-ethyl]-amide (A) The compound 1-(1-benzylpiperidin-4-yl)propan-2-one (intermediate XVIa) was prepared according to J. Bosch et al., *Tetrahedron* (1982) 38:2883. To a solution of intermediate XVIa (1.3 g, 5.63 mmol) in MeOH (20 ml) was added NH$_4$OAc (5.1 g, 67.56 mmol), and the mixture stirred at RT for 15 min., followed by addition of NaCNBH$_3$ (0.25 g, 3.94 mmol). Stirring was continued for 16 h, and solvent was removed under reduced pressure. The residue was dissolved in 6N HCl (20 ml), and washed twice with ether. The acidic aqueous solution was basified with 6N NaOH to pH 10 and extracted into CH$_2$Cl$_2$. The organic extract was dried with Na$_2$SO$_4$, filtered and concentrated to provide 1-(1-benzylpiperidin-4-yl)-2-aminopropane (intermediate XVIb, 1.27 g) as an oil.

(B) A solution of XVIb (1.29 g, 5.75 mmol) and (BOC)$_2$O (1.25 g, 5.75 mmol) in anhydrous THF (20 ml) was stirred at RT for 16 h. Solvent was removed under reduced pressure. The residue was partitioned between CH$_2$Cl$_2$ and water. The organic layer was dried with Na$_2$SO$_4$, filtered and concentrated. The residue was flash chromatographed (silica, 8% MeOH in CH$_2$Cl$_2$ with NH$_4$OH) to give 1-(1-benzylpiperidin-4-yl)-2-(butoxycarbonylamino)propane (intermediate XVIc, 1.64 g) as a white solid.

(C) A mixture of XVIc (1.6 g, 4.82 mmol) and 10% Pd/C (0.4 g) in EtOH (50 ml) was hydrogenated at 45 psi for 16 h. The reaction mixture was filtered through celite and the filtrate concentrated to give 1-(piperidin-4-yl)-2-(butoxycarbonylamino)propane (intermediate XVId, 1.049 g) as an oil.

(D) To a solution of XVId (0.4 g, 1.65 mmol) in anhydrous EtOH (8 ml) was added TEA (0.24 g, 2.39 mmol), followed by 2-chloropyrimidine (0.24 g, 2.05 mmol). The reaction mixture heated at reflux for 4 h, and solvent was removed under reduced pressure. The residue was dissolved in CH$_2$Cl$_2$, washed with H$_2$O, dried with Na$_2$SO$_4$, filtered, and concentrated. The residue was chromatographed (silica, 10% MeOH in CH$_2$Cl$_2$ with NH$_4$OH) to yield 1-(1-pyrimidin-2-yl-piperidin-4-yl)-2-(butoxycarbonylamino)propane (intermediate XVIe, 0.26 g) as yellow crystals.

(E) A solution of XVIe (0.25 g, 0.78 mmol), TFA (0.5 ml) in CH$_2$Cl$_2$ (5 ml) was stirred at RT for 16 h. Solvent and excess TFA were removed under reduced pressure. The residue was redissolved in CH$_2$Cl$_2$, and washed with ether. The aqueous layer was basified with NaOH to pH 10 and extracted into CH$_2$Cl$_2$. The organic solution was dried with K$_2$CO$_3$, filtered and concentrated to provide 1-(1-pyrimidin-2-ylpiperidin-4-yl)-2-amino-propane (intermediate XVIf, 0.163 g) as an oil.

(F) Intermediates XVIf and XIIId were condensed following the procedure of Example 12(D) to provide 2-(4-fluorophenyl)-4-propyl-oxazole-5-carboxylic acid [1-methyl-2-(4-pyrimidin-2-yl-piperidin-1-yl)-ethyl]-amide (compound 16). $M^{+H}$=452.

Example 17

Preparation of 2-(2-fluorophenyl)-4-phenyl-oxazole-5-carboxylic acid [1-methyl-2-(4-pyrid-2-yl-piperazin-1-yl)-ethyl]-amide (A) Proceeding as set forth in Example 1(A-C), but substituting 2-pyridinylamine for 6-chloro-2-pyridinylamine, the compound 1-methyl-2-[(4-pyridin-2-yl)piperazin-1-yl]-ethylamine (intermediate XVIIa) was prepared.

(B) 2-Fluorobenzoic acid (6 g, 42.8 mmole) was dissolved in 300 mL of anhydrous THF and the resulting reaction solution was cooled to 0° C. To this solution was added sodium hydride (1.88 g of a 60% oil dispersion, 47.1 mmole). The reaction mixture was allowed to warm to room temperature over 1 h. The THF was removed by evaporation before addition of 2-chloro-3-oxo-3-phenyl-propionic acid ethyl ester (9.7 g, 42.8 mmole) in 250 mL of ethanol. Reaction solution was warmed at reflux for 24 h. The ethanol was removed by evaporation and the resulting product was dissolved in water and extracted with toluene. The toluene was washed with 2 N aqueous $Na_2CO_3$, and saturated NaCl. The resulting toluene layer was concentrated and purified by chromatography (5-8% ethyl acetate in hexanes gradient) providing 2-fluoro-benzoic acid 1-ethoxycarbonyl-2-oxo-2-phenyl-ethyl ester (Intermediate XVIIb, 5.3 g, 38% yield)

(C) Intermediate XVII b (5.7 g, 17.4 mmole) was dissolved in 80 mL of acetic acid and 10.7 g of ammonium acetate (14 mmole) was added. The reaction mixture was warmed at reflux for 1 h. Solvent was removed by evaporation. Purification by chromatography (silica, 10% ethyl acetate in hexanes eluant) provided 2-(2-fluorophenyl)-4-phenyl-oxazole-5-carboxylic acid ethyl ester (Intermediate XVIIc, 2.73 g, 27% yield) $M^+H$ =312

(D) Intermediate XVIIc (1.44 g, 4.6 mmole) was dissolved in 30 mL THF and 2 mL of water. To the reaction solution was added 14 mL of 2N NaOH (aqueous) and the resulting reaction mixture was warmed at reflux for 4 h. The solvent was removed by evaporation to afford a white solid. The solid was washed with aqueous HCl (pH=1) and collected by filtration and dried under vacuum to give 2-(2-fluorophenyl)-4-phenyl-oxazole-5-carboxylic acid (Intermediate XVIId, 1.29 g, 98% yield)

(E) Intermediates XVIIa and XVIId were condensed following the procedure of Example 12(D) to provide the compound 2-(2-fluorophenyl)-4-phenyl-oxazole-5-carboxylic acid [1-methyl-2-(4-pyrid-2-yl-piperazin-1-yl)-ethyl]-amide (compound 17).

Example 18

Preparation of 2-(2-fluorophenyl)-4-(2-methylsulfanylethyl)-oxazole-5-carboxylic acid [1-methyl-2-(4-pyrimidin-2-yl-piperazin-1-yl)-ethyl]-amide Proceeding as set forth in Example 13, but substituting 2-fluorobenzoyl chloride for 2,4-difluorobenzoyl chloride, the compound 2-(2-fluorophenyl)-4-(2-methylsulfanylethyl)-oxazole-5-carboxylic acid [1-methyl-2-(4-pyrimidin-2-yl-piperazin-1-yl)-ethyl]-amide (compound 18) was prepared.

Example 19

Preparation of 2-(2-fluorophenyl)-4-(2-methylsulfonylethyl)-oxazole-5-carboxylic acid [1-methyl-2-(4-pyrimidin-2-yl-piperazin-1-yl)-ethyl]-amide Proceeding as set forth in Example 14, but substituting compound 18 for compound 12, the compound 2-(2-fluorophenyl)-4-(2-methylsulfonylethyl)-oxazole-5-carboxylic acid [1-methyl-2-(4-pyrimidin-2-yl-piperazin-1-yl)-ethyl]-amide (compound 19) was prepared.

Example 20

Preparation of 2,5-diphenyloxazole-4-carboxylic acid [1-methyl-2-(4-pyrimidin-2-yl-piperazin-1-yl)-ethyl]-amide (A) To a suspension of ethyl 2-amino-acetate (1.0 g, 7.16 mmol) in anhydrous $CH_2Cl_2$ (5 ml) was added TEA (1.82 g, 17.96 mmol). The reaction mixture was cooled in an ice bath, and a solution of benzoyl chloride (1.0 g, 7.17 mmol) in $CH_2Cl_2$ (2 ml) was added dropwise. After addition was completed, stirring was continued at RT for two more hours. The reaction mixture was washed with water, dried with $MgSO_4$, filtered, and concentrated. Column chromatography (silica, 30% EtOAc in hexanes) gave benzoylaminoacetic acid ethyl ester (intermediate XXa, 1.24 g) as a white solid.

(B) To a solution of intermediate XXa (0.62 g, 2.99 mmol) in anhydrous THF (10 ml) was added Lawesson's reagent (0.85 g, 2.09 mmol). The reaction mixture was heated at reflux for 1 h, and solvent was removed under reduced pressure. Column chromatography (silica, 25% EtOAc in hexanes) gave thiobenzoylaminoacetic acid ethyl ester (intermediate XXb, 0.48 g) as yellow solid.

(C) To a solution of intermediate XXb (0.24 g, 1.09 mmol) in $CH_2Cl_2$ (3 ml) at −78° C. was added $BF_3$ etherate (0.18 g, 1.2 mmol). The reaction mixture was stirred at 0° C. for 2 h before it was quenched with water (1 ml). The organic layer was washed with sat. $NaHCO_3$ solution, $H_2O$, dried with $Na_2SO_4$, filtered, and concentrated to yield (methylsulfanyl-phenyl-methyleneimino) acetic acid ethyl ester (intermediate XXc, 0.24 g) as yellow oil.

(D) To a solution of intermediate XXc (0.23 g, 0.97 mmol) in $CH_2Cl_2$ (1.5 ml) was added benzoyl chloride (0.82 g, 5.81 mmol) and TEA (0.59 g, 5.81 mmol) in that order. The reaction mixture was stirred at RT for 16 h. Saturated $NaHCO_3$ solution (2 ml) was added and stirring was continued for another hour. The organic layer was separated, washed with $H_2O$, dried over $MgSO_4$, filtered and concentrated. Column chromatography (silica, 10% EtOAc in hexanes) yielded 2,5-diphenyloxazole-4-carboxylic acid ethyl ester (intermediate XXd, 0.254 g) as pale yellow solid.

(E) To a solution of intermediate XXd (0.254 g, 0.87 mmol) in THF (6 mL) was added a solution of NaOH (0.34 g, 8.66 mmol) in $H_2O$ (3 ml). The reaction mixture was heated at 70° C. for 3 h. Most of the THF was removed under reduced pressure and the residue was acidified to pH 2 using 3N HCl. The solid precipitated out was collected and dried to provide 2,5-diphenyl-oxazole-4-carboxylic acid (intermediate XXe, 0.151 g) as white solid.

(F) Following the procedure set forth in Example 21(F), but substituting intermediate XXe for XXIe, the compound 2,5-diphenyloxazole-4-carboxylic acid [1-methyl-2-(4-pyrimidin-2-yl-piperazin-1-yl)-ethyl]-amide (compound 20) was prepared. $M^+H$=469.

(G) Similarly, following the procedure set forth in Example 20(F) but substituting 2-(2-fluorophenyl)-4-propyl-oxazole-5-carboxylic acid for XXe, the compound 2-(2-fluorophenyl)-4-propyl-oxazole-5-carboxylic acid [1-methyl-2-(4-pyrimidin-2-yl-piperizin-1-yl)ethyl]-amine (compound 23) was prepared.

Example 21

Preparation of 2-(2-fluorophenyl)-4-(4-morpholinyl-methyl)-oxazole-5-carboxylic acid [1-methyl-2-(4-pyrimidin-2-yl-piperazin-1-yl)-ethyl]-amide (A) To a homogeneous solution of L-alanine(5 g, 56.1 mmol) in acetone (90 ml) and 1N NaOH (90 ml) was added 2-fluorobenzoyl chloride (8.9 g, 56.1 mmol) dropwise. Basicity of the reaction was maintained by adding 1N NaOH periodically. After the addition of 2-fluorobenzoyl chloride was completed, the reaction mixture was acidified to pH 2 using 1N HCl. The oil that precipitated out was extracted into EtOAc, which was dried over $MgSO_4$, filtered, and concentrated to yield 2-(2-fluorobenzoylamino)propionic acid (intermediate XXIa, 3.92 g). Upon standing, more crystals of intermediate XXIa (2.3 g) precipitated from the acidic aqueous solution and were collected.

(B) A solution of intermediate XXIa (2.3 g, 10.9 mmol), and oxalyl dichloride (13.8 g, 108.9 mmol) in anhydrous THF (50 ml) was stirred at RT for 16 h and concentrated. The residue was taken up in toluene and concentrated again. This processes was repeated to ensure complete removal of excess oxalyl dichloride. To the cold residue (in an ice bath) was added TEA (1.66 g, 16.3 mmol) and anhydrous MeOH (70 ml). The reaction mixture was stirred at RT overnight and concentrated. Flash chromatography (silica, 10% EtOAc in hex) yielded 2-(2-fluorophenyl)-4-methyloxazole-5-carboxylic acid methyl ester (intermediate XXIb, 1.34 g) as a white solid.

(C) A solution of intermediate XXIb (489 mg, 2.08 mmol) and azobisisobutyronitrile (AIBN, 68 mg, 0.42 mmol) in $CCl_4$ (25 ml) was heated at reflux, and N-bromosuccinimide (NBS, 370 mg, 2.08 mmol) was added portionwise. The reaction mixture heated at reflux overnight and was washed with $H_2O$. The organic solution was dried over $MgSO_4$, filtered, and concentrated to yield a mixture of 2-(2-fluorophenyl)-4-bromomethyl-oxazole-5-carboxylic acid methyl ester (intermediate XXIc, 705 mg) and intermediate XXIb in a 7:3 ratio.

(D) To solution of morpholine (40 mg, 0.45 mmol) in $CH_2Cl_2$ (chilled in an ice bath) was added a solution of intermediate XXIc (140 mg, 0.45 mmol) and TEA (51 mg, 0.49 mmol). The reaction mixture was stirred at room temperature overnight and flash chromatographed (14% MeOH in $CH_2Cl_2$) yielded 2-(2-fluorophenyl)-4-morpholinomethyl-oxazole-5-carboxylic acid methyl ester (intermediate XXId, 60 mg) as pale yellow glass.

(E) To a solution of NaOH (75 mg, 1.87 mmol) in $H_2O$ (0.7 ml) was added a solution of intermediate XXId (60 mg, 0.19 mmol) in THF (1.5 ml). The reaction mixture was heated at 70° C. for 3 h and concentrated. The solution was adjusted to pH 1 with 3N HCl and concentrated to provide crude 2-(2-fluorophenyl)-4-morpholinomethyl-oxazole-5-carboxylic acid (intermediate XXIe) as an HCl salt.

(F) A solution of crude intermediate XXIe and intermediate XIIId (50 mg, 0.17 mmol), di-isopropyl-ethylamine (DIEA, 267 mg, 2.04 mmol) and 2-(1-H-benzotriazol-1-yl-)-1,1,3,3-tetramethyluronium hexafluorophosphate (HBTU, 64 mg, 0.17 mmol) in anhydrous THF (2.5 ml) was stirred at room temperature for 16 h. The reaction mixture was partitioned between EtOAc and $H_2O$. The organic layer was dried over $MgSO_4$, filtered and concentrated. PTLC (6% MeOH in $CH_2Cl_2$) provided 2-(2-fluorophenyl)-4-(4-morpholinylmethyl)-oxazole-5-carboxylic acid [1-methyl-2-(4-pyrimidin-2-yl-piperazin-1-yl)-ethyl]-amide (compound 21, 25 mg) as a white solid. $M^+H=510$.

(G) Similarly, proceeding as set forth above but substituting 1-methylpiperazine for morpholine, the compound 2-(2-fluorophenyl)-4-(1-methyl-piperazin-4-ylmethyl)-oxazole-5-carboxylic acid [1-methyl-2-(4-pyrimidin-2-yl-piperazin-1-yl)-ethyl]-amide (compound 22) was prepared.

Example 22

Preparation of 2-phenyl-4-(4-chlorophenyl)-thiazole-5-carboxylic acid [1-methyl-2-(4-pyrimidin-2-yl-piperazin-1-yl)-ethyl]-amide (A) To a suspension of dicyclohexylcarbodiimide polymer (128 mg, 0.1 mmol) supported in $CH_2Cl_2$ (1.5 ml) were added [4-(4-chlorophenyl)-2-phenyl-thiazol-5-yl]-acetic acid, (0.06 mmol) and hydroxybenzotriazole (HOBT, 0.085 mmol). The mixture was agitated at RT for 1 h. 1-methyl-2-(4-pyrimidin-2-yl-piperazin-1-yl)ethyl amine (0.05 mmole) in DMF solution (0.1 ml) was added. The mixture was agitated for 18 h at RT. The resin was filtered off and washed 3 times with dichloromethane. The product, 2-[4-(4-Chlorophenyl)-2-phenyl-thiazol-5-yl]-N-[1-methyl-2-(4-pyrimidin-2-yl-piperazin-1-yl)-ethyl]-acetamide (compound 25) was purified via preparative HPLC. $M^+=533$.

(B) Similarly, proceeding as set forth in part (A) above but substituting 3-(4,5-diphenyl-oxazol-2-yl)propionic acid for 2-phenyl-4-(4-chlorophenyl)-thiazole-5-carboxylic acid, the compound 4,5-diphenyloxazol-2-yl propionic acid [1-methyl-2-(4-pyrimidin-2-yl-piperizin-1-yl)ethyl]-amine (compound 26) was prepared. M+H=497

(C) Similarly, proceeding as set forth in part (A) above but substituting 2-methyl-4-phenyloxazol-5-yl acetic acid for 2-phenyl-4-(4-chlorophenyl)-thiazole-5-carboxylic acid, the compound 2-methyl-4-phenyl-oxazole-5-acetic acid [1-methyl-2-(4-pyrimidin-2-yl-piperizin-1-yl)ethyl]-amine (compound 27) was prepared. M+H=421

(D) Similarly, proceeding as set forth in part (A) above but substituting 2,4-diphenyl-thiazole-5-acetic acid for 2-phenyl-4-(4-chlorophenyl)-thiazole-5-carboxylic acid, the compound 2,4-diphenyl-thiazole-5-acetic acid [1-methyl-2-(4-pyrimidin-2-yl-piperizin-1-yl)ethyl]-amine (compound 28) was prepared. M+H=499

(E) Similarly, proceeding as set forth in part (A) above but substituting 2-(4-chloro-phenyl)-4-phenyl-oxazol-5-yl acetic acid for 2-phenyl-4-(4-chlorophenyl)-thiazole-5-carboxylic acid, the compound 2-(4-chlorophenyl)-4-phenyl-oxazole-5-acetic acid [1-methyl-2-(4-pyrimidin-2-yl-piperizin-1-yl)ethyl]-amine (compound 29) was prepared. M+H=533

(F) Proceeding as set forth in part (A) above but substituting 2-phenyl-4-trifluoromethyl-thiazole-5-carboxylic acid for 2-phenyl-4-(4-chlorophenyl)-thiazole-5-carboxylic acid, the compound 2-phenyl-4-trifluoromethyl-thiazole-5-carboxylic acid [1-methyl-2-(4-pyrimidin-2-yl-piperazin-1-yl)-ethyl]-amide (compound 30) was prepared. M+H=477

(G) Proceeding as set forth in part (A) above, but substituting 4-methyl-2-pyridin-2-yl-thiazole-5-carboxylic acid for 2-phenyl-4-(4-chlorophenyl)-thiazole-5-carboxylic acid and substituting intermediate XIIId and DIEA (0.03 mL) for 1-methyl-2-(4-pyrimidin-2-yl-piperazin-1-yl)ethyl amine, the compound 2-(pyrid-2-yl)-4-methyl-thiazole-5-carboxylic acid [1-methyl-2-(4-pyrimidin-2-yl-piperazin-1-yl)-ethyl]-amide (compound 31) was prepared. M+H=424

(H) Proceeding as set forth in part (G) above, but substituting 4-methyl-2-p-tolyl-thiazole-5-carboxylic acid for 4-methyl-2-pyridin-2-yl-thiazole-5-carboxylic acid, the compound 2-(4-methylphenyl)-4-methyl-thiazole-5-carboxylic acid [1-methyl-2-(4-pyrimidin-2-yl-piperazin-1-yl)-ethyl]-amide (compound 32) was prepared. M+H=437

(I) Proceeding as set forth in part (G) above, but substituting 2-(thiophen-2-yl)-4-methyl-thiazole-5-carboxylic acid for 4-methyl-2-pyridin-2-yl-thiazole-5-carboxylic acid, the compound 2-(thiophen-2-yl)-4-methyl-thiazole-5-carboxylic acid [1-methyl-2-(4-pyrimidin-2-yl-piperazin-1-yl)-ethyl]-amide (compound 33) was prepared. M+H=429

(J) Proceeding as set forth in part (A) above but substituting 5-methyl-1,3-diphenyl-1H-pyrazole-4-carboxylic acid for 2-phenyl-4-(4-chlorophenyl)-thiazole-5-carboxylic acid, the compound 5-methyl-1,3-diphenyl-1H-pyrazole-4-carboxylic acid [1-methyl-2-(4-pyrimidin-2-yl-piperazin-1-yl)-ethyl]-amide (compound 35) was prepared. M+H=482

Example 23

Preparation of 2,4-diphenyl-thiazole-5-carboxylic acid [1-methyl-2-(4-pyrimidin-2-yl-piperazin-1-yl)-ethyl]-amide (A) To a solution sulfuryl chloride (0.78 g, 5.78 mmol) in anhydrous $CH_2Cl_2$ (3 ml), was slowly added a solution of 3-oxo-3-phenylpropionic acid (1.09 g, 5.67 mmol) in anhydrous $CH_2Cl_2$ (10 ml) at −5° C., the mixture was stirred at room temperature for 2 h, partitioned between $CH_2Cl_2$, and water, and the organic phase was washed with brine, and dried over anhydrous sodium sulfate. After decanting from the drying agent, the organic solution was concentrated under reduced pressure to yield 2-chloro-3-oxo-3-phenylpropionic acid ethyl ester (intermediate XXIIIa, 1.255 g) as a yellow oil (97%).

(B) A solution of intermediate XXIIa (1.24 g, 5.47 mmol) and thiobenzamide (0.90 g, 6.56 mmol) in dry EtOH (10 ml) was heated at reflux for 2.5 h, evaporating most of the EtOH. The residue was partitioned between EtOAc and water, the organic phase was washed with brine, dried over anhydrous sodium sulfate, decanted, and the organic solution concentrated under reduced pressure. The residue was purified by silica gel chromatography (10% EtOAc in hexanes) to yield 2,4-diphenyl-thiazole-5-carboxylic acid ethyl ester (intermediate XXIIb, 1.16 g) as a white solid (68%). M+H=310.

(C) Following the procedure set forth in Example 20(E-F), but substituting intermediate XXIIIb for XXIe, the compound 2,4-diphenyl-thiazole-5-carboxylic acid [1-methyl-2-(4-pyrimidin-2-yl-piperazin-1-yl)-ethyl]-amide (compound 34) was prepared.

Example 24

Preparation of 5-propyl-1-phenyl-1H-pyrazole-4-carboxylic acid [1-methyl-2-(4-pyrimidin-2-yl-piperazin-1-yl)-ethyl]-amide (A) Similarly, proceeding as set forth in Example 22A above, but substituting 1-phenyl-5-propyl-1H-pyrazole-4-carboxylic acid for 2-phenyl-4-(4-chlorophenyl)-thiazole-5-carboxylic acid, the compound 5-propyl-1-phenyl-1H-pyrazole-4-carboxylic acid [1-methyl-2-(4-pyrimidin-2-yl-piperazin-1-yl)-ethyl]-amide (compound 36) was prepared. M+H=434

(B) Similarly, proceeding as set forth in Example 22A above but substituting 1-(3,5-di-chlorophenyl)-5-propyl-1H-pyrazole-4-carboxylic acid for 2-phenyl-4-(4-chlorophenyl)-thiazole-5-carboxylic acid, the compound 5-propyl-1-(3,5-dichlorophenyl)-1H-pyrazole-4-carboxylic acid [1-methyl-2-(4-pyrimidin-2-yl-piperazin-1-yl)-ethyl]-amide (compound 37) was prepared. M+H=502

(C) Similarly, proceeding as set forth in Example 22A above but substituting 1-(4-fluorophenyl)-5-propyl-1H-pyrazole-4-carboxylic acid for 2-phenyl-4-(4-chlorophenyl)-thiazole-5-carboxylic acid, the compound 5-propyl-1-(4-fluorophenyl)-1H-pyrazole-4-carboxylic acid [1-methyl-2-(4-pyrimidin-2-yl-piperazin-1-yl)-ethyl]-amide (compound 38) was prepared. M+H=502

(C) Similarly, proceeding as set forth in Example 22A above but substituting 1-(4-fluorophenyl)-5-propyl-1-H-pyrazole-4-carboxylic acid for 2-phenyl-4-(4-chlorophenyl)-thiazole-5-carboxylic acid, the compound 5-propyl-1-(4-fluorophenyl)-1H-pyrazole-4-carboxylic acid [1-methyl-2-(4-pyrimidin-2-yl-piperazin-1-yl)-ethyl]-amide (compound 38) was prepared. M+H=424

(D) Similarly, proceeding as set forth in Example 22A above but substituting 5-t-butyl-2-(4-fluorobenzyl)-2H-pyrazole-3-carboxylic acid for 2-phenyl-4-(4-chlorophenyl)-thiazole-5-carboxylic acid, the compound 5-t-butyl-2-(4-fluorobenzyl)-2H-pyrazole-3-carboxylic acid [1-methyl-2-(4-pyrimidin-2-yl-piperazin-1-yl)-ethyl]-amide (compound 39) was prepared. M+H=480

(E) Similarly, proceeding as set forth in Example 22A above but substituting 1-phenyl-5-(4-chlorophenyl)-1H-pyrazole-3-carboxylic acid for 2-phenyl-4-(4-chlorophenyl)-thiazole-5-carboxylic acid, the compound 1-phenyl-5-(4-chlorophenyl)-1H-pyrazole-3-carboxylic acid [1-methyl-2-(4-pyrimidin-2-yl-piperazin-1-yl)-ethyl]-amide (compound 40) was prepared. M+H=502

(F) Similarly, proceeding as set forth in Example 22A above but substituting 1-(4-fluoro-phenyl)-5-(4-chlorophenyl)-1H-pyrazole-3-carboxylic acid for 2-phenyl-4-(4-chlorophenyl)-thiazole-5-carboxylic acid, the compound 1-(4-fluorophenyl)-5-(4-chlorophenyl)-1H-pyrazole-3-carboxylic acid [1-methyl-2-(4-pyrimidin-2-yl-piperazin-1-yl)-ethyl]-amide (compound 41) was prepared. M+H=520

(G) Similarly, proceeding as set forth in Example 22A above but substituting 1-(4-fluoro-phenyl)-5-phenyl-1H-pyrazole-3-carboxylic acid for 2-phenyl-4-(4-chlorophenyl)-thiazole-5-carboxylic acid, the compound 1-(4-fluorophenyl)-5-phenyl-1H-pyrazole-3-carboxylic acid [1-methyl-2-(4-pyrimidin-2-yl-piperazin-1-yl)-ethyl]-amide (compound 42) was prepared. M+H=486

(H) Similarly, proceeding as set forth in Example 22A above but substituting 1-(4-methylphenyl)-5-phenyl-1H-pyrazole-3-carboxylic acid for 2-phenyl-4-(4-chlorophenyl)-thiazole-5-carboxylic acid, the compound 1-(4-methylphenyl)-5-phenyl-1H-pyrazole-3-carboxylic acid [1-methyl-2-(4-pyrimidin-2-yl-piperazin-1-yl)-ethyl]-amide (compound 43) was prepared. M+H=482

(I) Similarly, proceeding as set forth in Example 22A above but substituting 1-phenyl-5-(2-chlorophenyl)-1H-pyrazole-3-carboxylic acid for 2-phenyl-4-(4-chlorophenyl)-thiazole-5-carboxylic acid, the compound 1-phenyl-5-(2-chlorophenyl)-1H-pyrazole-3-carboxylic acid [1-methyl-2-(4-pyrimidin-2-yl-piperazin-1-yl)-ethyl]-amide (compound 44) was prepared. M+H=502

(J) Similarly, proceeding as set forth in Example 22A above but substituting 1-(4-sulf-amoylphenyl)-5-(4-chlorophenyl)-1H-pyrazole-3-carboxylic acid for 2-phenyl-4-(4-chloro-phenyl)-thiazole-5-carboxylic acid, the compound 1-(4-sulfamoylphenyl)-5-(4-chlorophenyl)-1H-pyrazole-3-carboxylic acid [1-methyl-2-(4-pyrimidin-2-yl-piperazin-1-yl)-ethyl]-amide (compound 45) was prepared. M+H=581

(K) Similarly, proceeding as set forth in Example 22A above but substituting 1-(4-chlorophenyl)-5-phenyl-1H-pyrazole-3-carboxylic acid for 2-phenyl-4-(4-chlorophenyl)-thiazole-5-carboxylic acid, the compound 1-(4-chlorophenyl)-5-phenyl-1H-pyrazole-3-carboxylic acid [1-methyl-2-(4-pyrimidin-2-yl-piperazin-1-yl)-ethyl]-amide (compound 46) was prepared. M+H=502

(L) Similarly, proceeding as set forth in Example 22A above but substituting 1,5-di-phenyl-1H-pyrazole-4-carboxylic acid for 2-phenyl-4-(4-chlorophenyl)-thiazole-5-carboxylic acid, the compound 1,5-diphenyl-1H-pyrazole-4-carboxylic acid [1-methyl-2-(4-pyrimidin-2-yl-piperazin-1-yl)-ethyl]-amide (compound 47) was prepared. M+H=468

(M) Similarly, proceeding as set forth in Example 22A above but substituting 1,5-bis(4-chlorophenyl)-1H-pyrazole-3-carboxylic acid for 2-phenyl-4-(4-chlorophenyl)-thiazole-5-carboxylic acid, the compound 1,5-bis(4-chlorophenyl) 1H-pyrazole-3-carboxylic acid [1-methyl-2-(4-pyrimidin-2-yl-piperazin-1-yl)-ethyl]-amide (compound 48) was prepared. M+H=536

(N) Similarly, proceeding as set forth in Example 22A above but substituting 1-(2-chlorophenyl)-5-phenyl-1H-pyrazole-3-carboxylic acid for 2-phenyl-4-(4-chlorophenyl)-thiazole-5-carboxylic acid, the compound 1-(2-chlorophenyl)-5-phenyl-1H-pyrazole-3-carboxylic acid [1-methyl-2-(4-pyrimidin-2-yl-piperazin-1-yl)-ethyl]-amide (compound 49) was prepared. M+H=502

(O) Similarly, proceeding as set forth in Example 22A above but substituting 1-(4-chlorophenyl)-5-propyl-1H-pyrazole-3-carboxylic acid for 2-phenyl-4-(4-chlorophenyl)-thiazole-5-carboxylic acid, the compound 1-(4-chlorophenyl)-5-propyl-1H-pyrazole-3-carboxylic acid [1-methyl-2-(4-pyrimidin-2-yl-piperazin-1-yl)-ethyl]-amide (compound 50) was prepared. M+H=468

(P) Similarly, proceeding as set forth in Example 22A above but substituting 1,3-di-phenyl-1H-pyrazole-4-carboxylic acid for 2-phenyl-4-(4-chlorophenyl)-thiazole-5-carboxylic acid, the compound 1,3-diphenyl-1H-pyrazole-4-carboxylic acid [1-methyl-2-(4-pyrimidin-2-yl-piperazin-1-yl)-ethyl]-amide (compound 51) was prepared. M+H=468

(Q) Similarly, proceeding as set forth in Example 22A above but substituting 2,5-di-phenyl-2H-pyrazole-3-carboxylic acid for 2-phenyl-4-(4-chlorophenyl)-thiazole-5-carboxylic acid, the compound 2,5-diphenyl-2H-pyrazole-3-carboxylic acid [1-methyl-2-(4-pyrimidin-2-yl-piperazin-1-yl)-ethyl]-amide (compound 52) was prepared. M+H=468

(R) Similarly, proceeding as set forth in Example 22A above but substituting 1,5-di-phenyl-1H-pyrazole-3-carboxylic acid for 2-phenyl-4-(4-chlorophenyl)-thiazole-5-carboxylic acid, the compound 1,5-diphenyl-1H-pyrazole-3-carboxylic acid [1-methyl-2-(4-pyrimidin-2-yl-piperazin-1-yl)-ethyl]-amide (compound 53) was prepared. M+H=468

(S) Similarly, proceeding as set forth in Example 22A above but substituting 1-(4-methylphenyl)-5-(2-chlorophenyl)-1H-pyrazole-3-carboxylic acid for 2-phenyl-4-(4-chloro-phenyl)-thiazole-5-carboxylic acid, the compound 1-(4-methylphenyl)-5-(2-chlorophenyl)-1H-pyrazole-3-carboxylic acid [1-methyl-2-(4-pyrimidin-2-yl-piperazin-1-yl)-ethyl]-amide (compound 54) was prepared. M+H=516

(T) Similarly, proceeding as set forth in Example 22G above but substituting 1-phenyl-3-(biphen-4-yl)-1H-pyrazole-4-carboxylic acid for 4-Methyl-2-pyridin-2-yl-thiazole-5-carboxylic acid, the compound 1-phenyl-3-(biphen-4-yl)-1H-pyrazole-4-carboxylic acid [1-methyl-2-(4-pyrimidin-2-yl-piperazin-1-yl)-ethyl]-amide (compound 55) was prepared. M+H=544

(U) Similarly, proceeding as set forth in Example 22G above but substituting 2-phenyl-5-isopropyl-2H-pyrazole-3-carboxylic acid for 4-Methyl-2-pyridin-2-yl-thiazole-5-carboxylic acid, the compound 2-phenyl-5-isopropyl-2H-pyrazole-3-carboxylic acid [1-methyl-2-(4-pyrimidin-2-yl-piperazin-1-yl)-ethyl]-amide (compound 56) was prepared. M+H=434

(V) Similarly, proceeding as set forth in Example 22G above but substituting 1-(2-tri-fluoromethyl-phenyl)-3-(pyridin-4-yl)-1H-pyrazole-4-carboxylic acid for 4-Methyl-2-pyridin-2-yl-thiazole-5-carboxylic acid, the compound 1-(2-tri-fluoromethyl-phenyl)-3-(pyridin-4-yl)-1H-pyrazole-4-carboxylic acid [1-methyl-2-(4-pyrimidin-2-yl-piperazin-1-yl)-ethyl]-amide (compound 57) was prepared. M+H=537

(W) Similarly, proceeding as set forth in Example 22G above but substituting 1-(4-meth-oxyphenyl)-5-phenyl-1H-pyrazole-3-carboxylic acid for 4-Methyl-2-pyridin-2-yl-thiazole-5-carboxylic acid, the compound 1-(4-methoxyphenyl)-5-phenyl-1H-pyrazole-3-carboxylic acid [1-methyl-2-(4-pyrimidin-2-yl-piperazin-1-yl)-ethyl]-amide (compound 58) was prepared. M+H=498

(X) Similarly, proceeding as set forth in Example 22G above but substituting 1-phenyl-3-(4-chlorophenyl)-1H-pyrazole-4-carboxylic acid for 4-Methyl-2-pyridin-2-yl-thiazole-5-carboxylic acid, the compound 1-phenyl-3-(4-chlorophenyl)1-H-pyrazole-4-carboxylic acid [1-methyl-2-(4-pyrimidin-2-yl-piperazin-1-yl)-ethyl]-amide (compound 59) was prepared. M+H=502

(Y) Similarly, proceeding as set forth in Example 22G above but substituting 1-phenyl-3-(4-fluorophenyl)-1H-pyrazole-4-carboxylic acid for 4-Methyl-2-pyridin-2-yl-thiazole-5-carboxylic acid the compound 1-phenyl-3-(4-fluorophenyl)-1H-pyrazole-4-carboxylic acid [1-methyl-2-(4-pyrimidin-2-yl-piperazin-1-yl)-ethyl]-amide (compound 60) was prepared. M+H=486

(Z) Similarly, proceeding as set forth in Example 22G above but substituting 1,5-bis(4-chlorophenyl)-1H-pyrazole-3-carboxylic acid for 4-Methyl-2-pyridin-2-yl-thiazole-5-carboxylic acid, and 1-methyl-2-(4-acetyl-piperazin-1-yl) ethyl amine for intermediate Vd, the compound 1,5-bis(4-chlorophenyl)-1H-pyrazole-3-carboxylic acid [1-methyl-2-(4-acetyl-piperazin-1-ethyl]-amide (compound 61) was prepared. M+H=500

(AA) Similarly, proceeding as set forth in Example 22G above but substituting 1-(2-chlorophenyl)-5-(4-methylphenyl)-1H-pyrazole-3-carboxylic acid for 4-Methyl-2-pyridin-2-yl-thiazole-5-carboxylic acid, and 1-methyl-2-(4-acetyl-piperazin-1-yl)ethyl amine for intermediate Vd, the compound 1-(2-chlorophenyl)-5-(4-methylphenyl)-1H-pyrazole-3-carboxylic acid [1-methyl-2-(4-acetyl-piperazin-1-yl)-ethyl]-amide (compound 62) was prepared. M+H=480

(BB) Similarly, proceeding as set forth in Example 22A above but substituting 1,3-di-phenyl-1H-pyrazol-4-yl acrylic acid for 2-phenyl-4-(4-chlorophenyl)-thiazole-5-carboxylic acid, the compound 1,3-diphenyl-1H-pyrazol-4-yl acrylic acid [1-methyl-2-(4-pyrimidin-2-yl-piperazin-1-yl)-ethyl]-amide (compound 64) was prepared. M+H=524

(CC) Similarly, proceeding as set forth in Example 22A above, but substituting 2-methyl-1,5-diphenyl-1H-pyrrole-3-carboxylic acid for 2-phenyl-4-(4-chlorophenyl)-thiazole-5-carboxylic acid, the compound 2-methyl-1,5-diphenyl-1H-pyrrole-3-carboxylic acid [1-methyl-2-(4-pyrimidin-2-yl-piperazin-1-yl)-ethyl]-amide (compound 65) was prepared. M+H=481

(DD) Similarly, proceeding as set forth in part (A) above, but substituting 2-methyl-1-(4-methylsulfanylphenyl)-5-phenyl-1H-pyrrole-3-carboxylic acid for 2-phenyl-4-(4-chlorophenyl)-thiazole-5-carboxylic acid, the compound 2-methyl-(4-methylsulfanylphenyl)-5-phenyl-1H-pyrrole-3-carboxylic acid [1-methyl-2-(4-pyrimidin-2-yl-piperazin-1-yl)-ethyl]-amide (compound 66) was prepared. M+H=527

(EE) Similarly, proceeding as set forth in Example 22A above but substituting 5-t-butyl-2-(2-methylbenzyl)-2H-pyrazole-3-carboxylic acid for 2-phenyl-4-(4-chlorophenyl)-thiazole-5-carboxylic acid, the compound 5-t-butyl-2-(2-methylbenzyl)-2H-pyrazole-3-carboxylic acid [1-methyl-2-(4-pyrimidin-2-yl-piperazin-1-yl)-ethyl]-amide (compound 67) was prepared. M+H=476

(FF) Similarly, proceeding as set forth in Example 22A above but substituting 1-(3-chlorophenyl)-5-(4-chlorophenyl)-1H-pyrazole-3-carboxylic acid for 2-phenyl-4-(4-chloro-phenyl)-thiazole-5-carboxylic acid, the compound 1-(3-chlorophenyl)-5-(4-chlorophenyl)-1H-pyrazole-3-carboxylic acid [1-methyl-2-(4-pyrimidin-2-yl-piperazin-1-yl)-ethyl]-amide (compound 68) was prepared. M+H=536

Example 25

Preparation of 2-(4-fluorophenyl)-5-phenyl-3H-imidazole-4-carboxylic acid [1-methyl-2-(4-pyrimidin-2-yl-piperazin-1-yl)-ethyl]-amide Proceeding as set forth in Example 23 above but substituting 2-(4-fluorophenyl)-5-phenyl-3H-imidazole-4-carboxylic acid for 5-methyl-1,3-diphenyl1-H-pyrazole-4-carboxylic acid, the compound 2-(4-fluorophenyl)-5-phenyl-3H-imidazole-4-carboxylic acid [1-methyl-2-(4-pyrimidin-2-yl-piperazin-1-yl)-ethyl]-amide (compound 63) was prepared.

Example 26

Preparation of 3,5-diphenyl-furan-2-carboxylic acid [1-methyl-2-(4-pyrimidin-2-yl-piperazin-1-yl)-ethyl]-amide (A) To a mixture of benzaldehyde (2.6 ml, 25.58 mmol) and acetophenone (6 ml, 51.44 mmol) in anhydrous benzene (3 ml), was added boron trifluoride diethyl etherate (8 ml, 63.13 mmol) at RT. The mixture was heated at reflux for 2 h, cooled to RT, acetone was added (5 ml), and the resulting dark red solution was poured into ether (250 ml). A dark yellow precipitate formed, which was isolated and redissolved in acetone (30 ml), ether was added until the yellow solid was formed, isolated and dried to provide 2,4,6-triphenyl-pyranylium (3.87 g, 48%, mw=309). To a suspension of 2,4,6-triphenyl-pyranylium (3.86 g, 12.5 mmol) in acetone (50 ml), was added a solution of Na$_2$CO$_3$ (1.7 g, 16 mmol) in H$_2$O (4.6 ml), and the mixture was stirred at RT for 2 h. To the reaction mixture, iodine (4.1 g, 16.1 mmol) was added, and the resulting mixture was stirred at RT overnight, then poured into a solution of sodium thiosulfate pentahydrate (40.0 g, 160 mmol) in water (250 ml), extracted with CH$_2$Cl$_2$. The organic phase was washed with brine, dried over anhydrous sodium sulfate, decanted, and the organic solution concentrated under reduced pressure. The residue was purified by silica gel chromatography (1% EtOAc in hexane) to provide (3,5-diphenylfuran-2-yl)-phenyl-methanone (intermediate XXVIa, 1.6 g, 19%) as a yellow solid.

(B) To a suspension of potassium t-butoxide (5.6 g, 50 mmol) in dioxane (25 ml) and water (0.27 ml), was added intermediate XXVIa. The mixture was stirred at RT for 30 min, poured into ice water (250 ml), and stirred for 1.5 h. The precipitate was isolated and redissolved in EtOAc, which was washed with water and brine, dried over anhydrous sodium sulfate, decanted, and the organic solution concentrated under reduced pressure. The residue was purified by silica gel chromatography (5% EtOAc in hexane) to yield 2,4-diphenylfuran (intermediate XXVIb, 0.99 g, 91%) as a pale yellow solid.

(C) To a solution of chlorosulfonyl isocyanate (0.45 ml, 5.16 mmol) in acetonitrile (15 ml) and CH$_2$Cl$_2$ (15 ml) was added dropwise a solution of intermediate XXVIb (0.748 g, 3.4 mmol) in CH$_2$Cl$_2$ (10 ml) at −78° C. The mixture was stirred at −78° C. for one h, and was then treated with a solution of N,N-dimethyl formamide (DMF, 1 ml, 14.1 mmol) in CH$_2$Cl$_2$ (1 ml). The resulting solution was stirred from −78° C. to −35° C. over 3.5 hours, at RT for 2 h, then poured into ice, partitioned between EtOAc and 5% aqueous NaHCO$_3$. The organic phase was washed with brine, dried over anhydrous sodium sulfate, decanted, and the organic solution concentrated under reduced pressure. The residue was purified by silica gel chromatography (2%, 6% EtOAc in hexane) to yield 3,5-diphenylfuran-2-carbonitrile (intermediate XXVIc, 0.512 g, 61%) as a yellow solid.

(D) A mixture of the intermediate XXVIc (0.14 g, 0.57 mmol) in MeOH (10 ml) and KOH (4.0 g, 71.3 mmol) in water (10 ml) was heated at reflux for 8 h, and cooled to RT. After most of the MeOH was removed, the pH of the aqueous solution was adjusted to acidic, and the solid was isolated and redissolved in EtOAc. The organic phase was washed with brine, dried over anhydrous sodium sulfate, decanted, and the organic solution concentrated under reduced pressure to provide 3,5-diphenylfuran-2-carboxylic acid (intermediate XXVId, 0.147 g, 98%) as a pale yellow solid. MW−1=263.

(E) Proceeding as set forth in Example 21(F), but substituting intermediate XXVId for intermediate XXIe, the compound 3,5-diphenyl-furan-2-carboxylic acid [1-methyl-2-(4-pyrimidin-2-yl-piperazin-1-yl)-ethyl]-amide (compound 81) was prepared. M$^{+H}$=468.

(F) A suspension of 2,5-diphenylfuran-3-carbonitrile (0.87 g, 3.56 mmol) in ethylene glycol and 3M NaOH (10 ml) was heated at reflux for 3 days. Water was added to the reaction mixture and extracted into CH$_2$Cl$_2$. The organic layer was dried with MgSO$_4$, filtered and concentrated to provide 2,5-diphenylfuran-3-carboxylic acid (intermediate XXVIf, 900 mg) as white solid.

(G) Proceeding as set forth in part (E) above, but substituting intermediate XXVIf for intermediate XXVId, the compound 2,5-diphenyl-furan-3-carboxylic acid [1-methyl-2-(4-pyrimidin-2-yl-piperazin-1-yl)-ethyl]-amide (compound 80) was prepared. M$^+$H=468.

(H) Similarly, proceeding as set forth in part (E) above, but substituting 1-methyl-2-(4-acetyl-piperazin-1-yl)ethyl amine for intermediate XIIId, the compound 3,5-diphenyl-furan-2-carboxylic acid [1-methyl-2-(4-acetyl-piperazin-1-yl)-ethyl]-amide (compound 78) was prepared. M+H=432

Example 27

Preparation of 1-(2,4-difluorophenyl)-5-phenyl-1H-[1,2,3]triazole-4-carboxylic acid [1-methyl-2-(4-pyrimidin-2-yl-piperazin-1-yl)-ethyl]-amide (A) Proceeding as set forth in Example 22(A), but substituting 1-(2,4-difluorophenyl)-5-phenyl-1H-[1,2,3]triazole-4-carboxylic acid for 2-phenyl-4-(4-chlorophenyl)-thiazole-5-carboxylic acid, the compound 1-(2,4-difluorophenyl)-5- phenyl1-H-[1,2,3]triazole-4-carboxylic acid [1-methyl-2-(4-pyrimidin-2-yl-piperazin-1-yl)-ethyl]-amide (compound 70) was prepared. M+H=505

(B) Proceeding as set forth in Example 22(A), but substituting 1-(3-trifluoromethyl-5-phenyl-1H-[1,2,3]triazole-4-carboxylic acid for 2-phenyl-4-(4-chlorophenyl)-thiazole-carboxylic acid, the compound 1-(3-trifluoromethylphenyl)-5-phenyl-1H-[1,2,3]triazole-4-carboxylic acid [1-methyl-2-(4-pyrimidin-2-yl-piperazin-1-yl)-ethyl]-amide (compound 71) was prepared. M+H=537

(C) Proceeding as set forth in Example 22(A), but substituting 1,5-diphenyl1H-[1,2,4]-triazole-3-carboxylic acid for 2-phenyl-4-(4-chlorophenyl)-thiazole-5-carboxylic acid, the compound 1,5-diphenyl-1H-[1,2,4]triazole-3-carboxylic acid [1-methyl-2-(4-pyrimidin-2-yl-piperazin-1-yl)-ethyl]-amide (compound 72) was prepared. M+H=469

(D) Proceeding as set forth in Example 22(A), but substituting 1,5-diphenyl-1H-[1,2,3]-triazole-4-carboxylic acid for 2-phenyl-4-(4-chlorophenyl)-thiazole-5-carboxylic acid, the compound 1,5-diphenyl-1H-[1,2,3]triazole-4-carboxylic acid [1-methyl-2-(4-pyrimidin-2-yl-piperazin-1-yl)-ethyl]-amide (compound 82) was prepared. M+H=469

(E) Proceeding as set forth in Example 22(A), but substituting 5-methyl-2-phenyl-furan-3-carboxylic acid for 2-phenyl-4-(4-chlorophenyl)-thiazole-5-carboxylic acid, the compound 5-methyl2-phenyl-furan-3-carboxylic acid [1-methyl-2-(4-pyrimidin-2-yl-piperazin-1-yl)-ethyl]-amide (compound 69) was prepared. M+H=406

(F) Proceeding as set forth in Example 22(G), but substituting 2-methyl-5-phenyl-furan-3-carboxylic acid for 4-methyl-2-pyridin-2-yl-thiazole-5-carboxylic acid, the compound 2-methyl-5-phenyl-furan-3-carboxylic acid [1-methyl-2-(4-pyrimidin-2-yl-piperazin-1-yl)-ethyl]-amide (compound 73) was prepared. M+H=406

(G) Proceeding as set forth in Example 22(G), but substituting 5-(4-fluorophenyl)-furan-2-carboxylic acid for 4-methyl-2-pyridin-2-yl-thiazole-5-carboxylic acid, the compound 5-(4-fluorophenyl)-furan-2-carboxylic acid [1-methyl-2-(4-pyrimidin-2-yl-piperazin-1-yl)-ethyl]-amide (compound 74) was prepared. M+H=410

(H) Proceeding as set forth in Example 22(G), but substituting 2-(N,N-diethylamino-methyl)-5-phenyl-furan-3-carboxylic acid for 4-methyl-2-pyridin-2-yl-thiazole-5-carboxylic acid, the compound 2-(N,N-diethylaminomethyl)-5-phenyl-furan-3-carboxylic acid [1-methyl-2-(4-pyrimidin-2-yl-piperazin-1-yl)-ethyl]-amide (compound 75) was prepared. M+H=477

(I) Similarly, proceeding as set forth in part (H) above, but substituting 2-methyl-1-(3-morpholin-4-ylpropyl)-5-phenyl-1H-pyrrole-3-carboxylic acid for 2-(N,N-diethylaminomethyl)-5-phenyl-furan-3-carboxylic acid, the compound 2-methyl-1-(3-morpholin-4-ylpropyl)-5-phenyl-1H-pyrrole-3-carboxylic acid [1-methyl-2-(4-pyrimidin-2-yl-piperazin-1-yl)-ethyl]-amide (compound 76) was prepared. M+H=532

(J) Similarly, proceeding as set forth in part (H) above, but substituting 2-methyl-1-(4-methylsulfanylphenyl)-5-phenyl-1H-pyrrole-3-carboxylic acid for 2-(N,N-diethylaminomethyl)-5-phenyl-furan-3-carboxylic acid, the compound 2-methyl-1-(4-methylsulfanylphenyl)-5-phenyl-1H-pyrrole-3-carboxylic acid [1-methyl-2-(4-pyrimidin-2-yl-piperazin-1-yl)-ethyl]-amide (compound 77) was prepared. M+H=491

(K) Proceeding as set forth in Example 22(A), but substituting 2-methyl-5-(4-chlorophenyl)-furan-3-carboxylic acid for 2-phenyl-4-(4-chlorophenyl)-thiazole-5-carboxylic acid, the compound 2-methyl-5-(4-chlorophenyl)-furan-3-carboxylic acid [1-methyl-2-(4-pyrimidin-2-yl-piperazin-1-yl)-ethyl]-amide (compound 79) was prepared. M+H=440

Example 28

Preparation of 3-(2-fluorophenyl)-1-methyl-1H-thieno[2,3-c]pyrazole-5-carboxylic acid [1-methyl-2-(4-thioacetyl-piperazin-1-yl)-ethyl]-amide (A) To a solution of ethyl-2-fluorobenzoylacetate (4.3 ml, 24 mmol) in EtOH (48 ml) was added methylhydrazine (1.32 ml, 25 mmol) under $N_2$ at RT. The reaction was heated at reflux for 18 h. The mixture was then evaporated, and the off white solid residue taken up in hot EtOAc. The mixture was cooled down, and the white solid not dissolved was collected via filtration and washed with hexane, then dried under reduced pressure to yield 5-(2-fluorophenyl)-2-methyl-2H-pyrazol-3-ol (intermediate XXVIIIa, 3.54 g, 77% yield). $M^+$=193.

(B) To DMF (2.32 ml, 30 mmol) at 0° C. under $N_2$, phosphorus oxychloride (6.52 ml, 70 mmol) was added dropwise over 10 min. The reaction was stirred for 20 min at 0° C. (phosphorus oxychloride tends to freeze, so the ice bath was removed to let the reaction stir: it was never allowed over 10° C.). Intermediate XXVIIIa was added in one portion and the mixture stirred at reflux temperature for 30 min. The reaction was cooled down at RT, poured on ice, and quenched with NaOH (15% aqueous). The mixture was acidified to reach pH 6-7, and extracted 3× with $CH_2Cl_2$. The combined organic layers were washed with brine, dried over sodium sulfate, and evaporated. The crude mixture was purified via flash chromatography, affording 5-chloro-3-(2-fluorophenyl)-1-methyl-1H-pyrazole-3-carbaldehyde (intermediate XXVIIIb, 1.6 g, 67% yield) as a white solid. M+=239.

(C) To a solution of finely ground KOH (753 mg, 13 mmol) in a mixture of MeOH (4.5 ml) and water (1.1 ml), thioglycolic acid (0.349 ml, 5 mmol) was added, followed by intermediate XXVIIIb (800 mg, 3.4 mmol) at RT. The reaction mixture was heated at reflux for 3 h. The solvent was evaporated, and the off white solid residue taken up in hot water and filtered. The filtrate was cooled down at RT, and acidified with HCl (6N) to pH 3. The white solid precipitated, and was filtered and washed with water and hexane. It was dried at 40° C. under reduced pressure to yield 3-(2-fluorophenyl)-1-methyl-1H-thieno[2,3-c]pyrazole-5-carboxylic acid (intermediate XXVIIIc, 926 mg, 92% yield).

(D) Following the procedure set forth in Example 4 but substituting intermediate XXVIIIc for intermediate If, the compound 3-(2-fluorophenyl)-1-methyl-1H-thieno[2,3-c]pyrazole-5-carboxylic acid [1-methyl-2-(4-thioacetyl-piperazin-1-yl)-ethyl]-amide (compound 85, 22% yield) was obtained as a yellow foam. $M^+$=460.

(E) Proceeding as set forth in part D above, but substituting 1-Methyl-3-phenyl1H-thieno[2,3-c]pyrazole-5-carboxylic acid for intermediate XXVIIIc, the compound 3-phenyl-1-methyl1H-thieno[2,3-c]pyrazole-5-carboxylic acid [1-methyl-2-(4-thioacetyl-piperazin-1-yl)-ethyl]-amide (compound 83, 23% yield) was obtained as a white foam. $M^+$=442.

(F) Proceeding as set forth in part (E) above, but substituting 1-methyl-2-(4-pyrimidin-2-yl-piperazin-1-yl)ethyl amine 2HCl (intermediate XIIId) for [1-methyl-2-(4-thioacetyl-piperazin-1-yl)-ethyl]-amine and using DMF as the solvent, the compound 3-phenyl-1-methyl-1H-thieno[2,3-c]pyrazole-5-carboxylic acid [1-methyl-2-(4-pyrimidin-2-yl-piperazin-1-yl)-ethyl]-amide (compound 89, yield). M+H=462

(G) Proceeding as set forth in part (E) above, but substituting [1-methyl-2-(4-acetyl-piperazin-1-yl)-ethyl]-amine for [1-methyl-2-(4-thioacetyl-piperazin-1-yl)-ethyl]-amine, the compound 3-phenyl-1-methyl-1H-thieno[2,3-c]pyrazole-5-carboxylic acid [1-methyl-2-(4-acetyl-piperazin-1-yl)-ethyl]-amide (compound 91) M$^+$=426.

(H) Proceeding as set forth in part (E) above, but substituting [1,1-dimethyl-2-(4-pyrimidin-2-yl-piperazin-1-yl)-ethyl]-amine for [1-methyl-2-(4-thioacetyl-piperazin-1-yl)-ethyl]-amine, the compound 3-phenyl-1-methyl-1H-thieno[2,3-c]pyrazole-5-carboxylic acid [1,1-di-methyl-2-(4-pyrimidin-2-yl-piperazin-1-yl)-ethyl]-amide (compound 90) was obtained. M+H=476

(I) Proceeding as set forth in part (E) above, but substituting intermediate IIIc for [1-methyl-2-(4-thioacetyl-piperazin-1-yl)-ethyl]-amine, the compound 3-(2-fluorophenyl)-1-methyl-1H-thieno[2,3-c]pyrazole-5-carboxylic acid [1-methyl-2-(4-thiazol-2-yl-piperazin-1-yl)-ethyl]-amide (compound 84) was obtained as a white foam in 86% yield. M$^+$=467.

(J) Proceeding as set forth in part (C) above, but substituting ethylhydrazine for methyl-hydrazine, the acid 3-phenyl-1-ethyl-1H-thieno[2,3-c]pyrazole-5-carboxylic acid (Intermediate XXVIIIj) was obtained. Proceeding as set forth in part (F), but substituting Intermediate XXVIIIj for 1-Methyl-3-phenyl-1H-thieno[2,3-c]pyrazole-5-carboxylic acid, the compound 3-phenyl-1-ethyl-1H-thieno[2,3-c]pyrazole-ar-boxylic acid [1-methyl-2-(4-pyrimidin-2-yl-piperazin-1-yl)-ethyl]-amide (compound 86) was obtained as a white powder (yield 48%, mp 64-68.5° C. M+=476).

(K) Proceeding as set forth in part (D) above, but substituting [1-methyl-2-(4-acetyl-piperazin-1-yl)-ethyl]-amine for [1-methyl-2-(4-thioacetyl-piperazin-1-yl)-ethyl]-amine, the compound 3-(2-fluorophenyl)-1-methyl-1H-thieno[2,3-c]pyrazole-5-carboxylic acid [1-methyl-2-(4-acetyl-piperazin-1-yl)-ethyl]-amide (compound 87) was obtained (82% yield, M+=444).

(L) Proceeding as set forth in part (J) above, but substituting ethyl-2-methylbenzoyl-acetate for ethyl-2-fluorobenzoylacetate, the compound 3-(2-methylphenyl)-1-ethyl-1H-thieno-[2,3-c]pyrazole-5-carboxylic acid [1-methyl-2-(4-pyrimidin-2-yl-piperazin-1-yl)-ethyl]-amide (compound 88) was obtained as a white powder (yield 30%, mp 89-93° C., M+=476).

(M) Proceeding as set forth in part (F) above, but substituting 1-Phenyl-3-methyl-1H-thieno[2,3-c]pyrazole-5-carboxylic acid for 1-Methyl-3-phenyl-1H-thieno[2,3-c]pyrazole-5-carboxylic acid, the compound 3-methyl-1-phenyl-1H-thieno[2,3-c]pyrazole-5-carboxylic acid [1methyl-2-(4-pyrimidin-2-yl-piperazin-1-yl)-ethyl]-amide (compound 92) was obtained. M+H=462

(N) Proceeding as set forth in part (D) above, but substituting intermediate Vd for [1-methyl-2-(4-thioacetyl-piperazin-1-yl)-ethyl]-amine, the compound 3-(2-fluorophenyl)-1-methyl-1H-thieno[2,3-c]pyrazole-5-carboxylic acid [1-methyl-2-(4-pyrimidin-2-yl-piperazin-1-yl)-ethyl]-amide (compound 96) was obtained.

Example 29

Preparation of (R)-1-methyl-3-phenyl-1H-thieno[2,3-c]pyrazole-5-carboxylic acid [1-methyl-2-(4-thioacetyl-piperazin-1-yl)-ethyl]-amide (A) (R)-(1-methyl-2-oxo-ethyl)-carbamic acid tert-butyl ester (1.85 g, 10.7 mmole) and acetyl piperazine (1.53 g, 12 mmole) were combined in dichloroethane (125 mL). NaBH(OAc)$_3$ (4.53 g. 21 mmole) was added. The resultant reaction solution was stirred at room temperature for 20 h. An equal volume of saturated NaHCO$_3$ was added. The aqueous phase was extracted 3 times with CH$_2$Cl$_2$. The combined organic extracts were washed with saturated NaCl, dried over Na$_2$SO$_4$ and concentrated under vacuum. Purification by silica chromatography (5% methanol in CH$_2$Cl$_2$ provided (R)-[2-(4-acetylpiperazin-1-yl)-1-methyl-ethyl]-carbamic acid tert-butyl ester (Intermediate XXIXa, 2.6 g)

(B) Intermediate XXIXa (2.6 g) was dissolved in 80 mL of CH$_2$Cl$_2$. TFA (10 mL) was added. The reaction solution was stirred at room temperature for 2 h to afford (R)-1-[4-(2-aminopropyl)-piperazin-1-yl]-ethanone (Intermediate XXIXb, 100% yield)

(C) To a solution of 1-methyl-3-phenyl1H-thieno[2,3-c]pyrazole-5-carboxylic acid (1 g, 4 mmole) in anhydrous THF (60 mL) was added HBTU (1.5 g, 4 mmol), intermediate XXIXd (4 mmol) in THF (8 mL) and DIEA (4 mL). The reaction mixture was stirred at room temperature 18 h before concentration. Purification by flash chromatography 5% methanol in CH2Cl2 afforded (R)-1-methyl-3-phenyl-1H-thieno[2,3-c]pyrazole-5-carboxylic acid [2-(4-acetyl-piperazin-1-yl)-1-methyl-ethyl]-amide (Compound 93, 1.13 g). Compound 93 was converted to the oxylate salt (1.37 g). M+=426, $^1$H nmr αD(MeOH, 1.0)=−95.2, mp 133.9-139.9° C.

(D) Proceeding as set forth in part (A-C) above, but substituting (S)-(1-methyl-2-oxo-ethyl)-carbamic acid tert-butyl ester (R)-(1-methyl-2-oxo-ethyl)-carbamic acid tert-butyl ester, the compound (S)-1-methyl-3-phenyl-1H-thieno[2,3-c]pyrazole-5-carboxylic acid [2-(4-acetyl- piperazin-1-yl)-1-methyl-ethyl]-amide (compound 94, 0.7 g) was obtained. Compound 94 was converted to the oxylate salt (0.6 g). M+=426, $^1$H nmr: αD(MeOH, 1.0)=+94.5, mp 133.5-140.1° C.

(E) Proceeding as set forth in part C above, but substituting 1-methyl-3-(2-fluorophenyl)-1H-thieno[2,3-c]pyrazole-5-carboxylic acid for 1-methyl-3-phenyl-1H-thieno[2,3-c]pyrazole-5-carboxylic acid, the compound (R)-1-methyl-3-(2-fluorophenyl)-1H-thieno[2,3-c]pyrazole-5-carboxylic acid [2-(4-acetyl-piperazin-1-yl)-1-methyl-ethyl]-amide (Compound 95) was prepared. M+H=444

Example 30

Preparation of 1-methyl-3-phenyl-1H-indazole-5-carboxylic acid [1-methyl-2-(4-acetyl-piperazin-1-yl)-ethyl]-amide (A) To a solution of phenylmagnesium chloride (5.5 ml, 11 mmol, 2M in THF), 5-bromo-2-fluorobenzaldyde (2.03 g, 10 mmol) was added at −78° C. under N$_2$. The reaction was allowed to warm up to RT and stirred at RT for 18 h. The milky suspension was poured into a saturated solution of NH$_4$Cl and extracted 3× with EtOAc. The organic layers were combined, dried over sodium sulfate, and evaporated. The crude mixture was purified via flash chromatography affording (5-bromo-2-fluorophenyl)-phenyl-methanol (intermediate XXXa, 2.235 g, 80% yield) as a colorless oil. M$^+$=281.

(B) To a suspension of pyridinium chlorochromate (166 mg, 0.769 mmol) in CH$_2$Cl$_2$ (36 ml), a solution of intermediate XXXa (180 mg, 0.641 mmol) in CH$_2$Cl$_2$ (4 ml) was added at RT under N$_2$. The reaction was stirred for 4 h at RT, then Et$_2$O (25 ml) was added and the mixture filtered on a plug of fluorisyl. The filtrate was evaporated and the crude residue was purified via flash chromatography to provide (5-bromo-2-fluorophenyl)-phenyl-methanone (intermediate XXXb, 150 mg, 83% yield) of as a colorless oil. $M^+=279$.

(C) A solution of intermediate XXXb (150 mg, 0.538 mmol) in methyl hydrazine (1.5 ml) was heated at reflux for 3 h. The reaction was cooled down and poured into ice water. The precipitate was not suitable to filtration, so the mixture was extracted 3× with EtOAc. The organic layers were combined, dried and evaporated. The crude product was purified via flash chromatography, affording 5-bromo-1-methyl-3-phenyl-1H-indazole (intermediate XXXc, 125 mg, 81% yield) as a white solid. M+=287.

(D) To a solution of intermediate XXXc (123 mg, 0.429 mmol) in THF (3 ml) at −78° C. under $N_2$ was added butyl-lithium (Bu-Li, 321 μl, 1.6 M in hexane). The orange colored solution was stirred at −78° C. under nitrogen for 10 min, then dry $CO_2$ was bubbled trough the solution for 20 min until it discolored. The reaction was allowed to rise to RT, the solvent evaporated, and water added to the residue. HCl (1M) was added to the mixture until pH 2-3 was reached. A white precipitate formed. The solid was filtered and dried, affording 1-methyl-3-phenyl-1H-indazole-5-carboxylic acid (intermediate XXXd, 72 mg, 67% yield). $M^+=253$.

(E) Following the procedure set forth in Example 24(Z) but substituting intermediate XXXc for 1,5-bis(4-chlorophenyl)-1H-pyrazole-3-carboxylic acid, the compound 1-methyl-3-phenyl-1H-indazole-5-carboxylic acid [1-methyl-2-(4-acetyl-piperazin-1-yl)-ethyl]-amide (compound 97, 65% yield, mp=98.8-100.5° C., M+=420) was produced as a white foam.

(F) To a solution of XXXb (976 mg, 3.5 mmol) in EtOH (4 ml) was added hydrazine hydrate (204 μl, 4.2 mmol). The reaction was heated at reflux for 2 h, and stirred at RT for 18 h. The solvent was evaporated, and the residue partitioned between water and EtOAc, the organic layer was separated and the aqueous layer was extracted twice with EtOAc. The combined organic layers were dried over sodium sulfate and evaporated. The crude material was purified via flash chromatography, affording 5-bromo-3-phenyl-1H-indazole (intermediate XXXf, 320 mg, 33% yield) as a white solid. $M^+=273$.

(G) To a solution of intermediate XXXf (136 mg, 0.5 mmol) in EtOAc (3 ml), trimethyl oxonium tetrafluoroborate (96 mg, 0.65 mmol) was added at RT under $N_2$. The reaction mixture was stirred at RT for 3 h, and the milky suspension partitioned between a saturated solution of $NaHCO_3$ and EtOAc. The organic layer was separated and the aqueous fraction was extracted twice with EtOAc. The combined organic layers were dried over sodium sulfate and evaporated. The crude residue was purified via flash chromatography, affording 5-bromo-3-phenyl-2-methyl-1H-indazole (intermediate XXXg, 120 mg, 84% yield) as a white solid. $M^+=287$.

(H) To a solution of intermediate XXXg (120 mg, 0.418 mmol) in THF (4 ml), Bu-Li (314 μl, 1.6 M in hexane) was added at −78° C. under $N_2$. The reaction mixture was stirred at −78° C. for 5 min, and then dry $CO_2$ was bubbled through the reaction mixture for 15 min, until discoloration occurred. The reaction was warmed up to RT and the solvent evaporated. The crude lithium carboxylate (intermediate XXXh) was used in part (I) below. $M^+=253$.

(I) Following the procedure set forth in part (E) above, but substituting intermediate XXXh for intermediate XXXc, the compound 2-methyl-3-phenyl-1H-indazole-5-carboxylic acid [1-methyl-2-(4-acetyl-piperazin-1-yl)-ethyl]-amide (compound 98) was prepared. The product was purified by preparative HPLC, resulting in a trifluoroacetate salt in 7% yield. M+=420

Example 31

Preparation of 3-phenyl-1H-indole-2-carboxylic acid [1-methyl-2-(4-pyrimidin-2-yl-piperazin-1-yl)-ethyl]-amide (A) Proceeding as set forth in Example 28(F) above, but substituting 3-phenyl-1H-indole-2-carboxylic acid for 1-methyl-3-phenyl-1H-thieno[2,3-c]pyrazole-5-carboxylic acid, the compound 3-phenyl-1H-indole-2-carboxylic acid [1-methyl-2-(4-pyrimidin-2-yl-piperazin-1-ethyl]-amide (compound 99) was obtained. M+H=441

(B) Proceeding as set forth in Example 28(F) above, but substituting 5,7-diphenyl-pyrazolo[1,5-a]pyrimidine-2-carboxylic acid for 1-methyl-3-phenyl-1H-thieno[2,3-c]pyrazole-5-carboxylic acid, the compound 5,7-diphenyl-pyrazolo[1,5-a]pyrimidine-2-carboxylic acid [1-methyl-2-(4-pyrimidin-2-yl-piperazin-1-yl)-ethyl]-amide (compound 100) was obtained. M+H=519

(C) Proceeding as set forth in Example 28(F) above, but substituting 1-benzyl-1H-indole-3-carboxylic acid for 1-methyl-3-phenyl-1H-thieno[2,3-c]pyrazole-5-carboxylic acid, the compound 1-benzyl-1H-indole-3-carboxylic acid [1-methyl-2-(4-pyrimidin-2-yl-piperazin-1-yl)-ethyl]-amide (compound 101) was obtained. M+H=455

(D) Proceeding as set forth in Example 28(F) above, but substituting 5-methoxy-2-methyl-benzofuran-3-carboxylic acid for 1-methyl-3-phenyl-1H-thieno[2,3-c]pyrazole-5-carboxylic acid, the compound 5-methoxy-2-methyl-benzofuran-3-carboxylic acid [1-methyl-2-(4-pyrimidin-2-yl-piperazin-1-yl)-ethyl]-amide (compound 102) was obtained. M+H=410

(E) Proceeding as set forth in Example 28(F) above, but substituting 5-phenyl-7-trifluoromethyl-pyrazolo[1,5-a]pyrimidine-3-carboxylic acid for 1-methyl-3-phenyl-1H-thieno[2,3-c]pyrazole-5-carboxylic acid, the compound 5-phenyl-7-trifluoromethyl-pyrazolo[1,5-a]pyrimidine-3-carboxylic acid [1-methyl-2-(4-pyrimidin-2-yl-piperazin-1-yl)-ethyl]-amide (compound 103) was obtained. M+H=511

(F) Proceeding as set forth in Example 28(F) above, but substituting 5-(4-methoxy-benzyl)-4-oxo-4,5,6,7-tetrahydropyrazolo[1,5-a]pyrazine-2-carboxylic acid for 1-methyl-3-phenyl-1H-thieno[2,3-c]pyrazole-5-carboxylic acid, the compound 5-(4-methoxybenzyl)-4-oxo-4,5,6,7-tetrahydropyrazolo[1,5-a]pyrazine-2-carboxylic acid [1-methyl-2-(4-pyrimidin-2-yl-piperazin-1-yl)-ethyl]-amide (compound 105) was obtained. M+H=505

(G) Proceeding as set forth in Example 28(F) above, but substituting 5-(thiophen-2-yl-methyl)-4-oxo-4,5,6,7-tetrahydropyrazolo[1,5-a]pyrazine-2-carboxylic acid for 1-methyl-3-phenyl-1H-thieno[2,3-c]pyrazole-5-carboxylic acid, the compound 5-(thiophen-2-ylmethyl)-4-oxo-4,5,6,7-tetrahydropyrazolo[1,5-a]pyrazine-2-carboxylic acid [1-methyl-2-(4-pyrimidin-2-yl-piperazin-1-yl)-ethyl]-amide (compound 106) was obtained. M+H=481

(H) Proceeding as set forth in Example 28(F) above, but substituting 4-oxo-3-(3-tri-fluoromethylphenyl)-3,4-dihydro-phthalazine-1-carboxylic acid for 1-methyl-3-phenyl-1H-thieno[2,3-c]pyrazole-5-carboxylic acid, the compound 4-oxo-3-(3-trifluoromethylphenyl)-3,4-dihydro-phthalazine-1-carboxylic acid [1-methyl-2-(4-pyrimidin-2-yl-piperazin-1-yl)-ethyl]-amide (compound 107) was obtained. M+H=538

(I) Proceeding as set forth in Example 28(F) above, but substituting 3-methyl-2,3-benzofuran-2-carboxylic acid for 1-methyl-3-phenyl-1H-thieno[2,3-c]pyrazole-5-carboxylic acid, the compound 3-methyl-2,3-benzofuran-2-carboxylic acid [1-methyl-2-(4-pyrimidin-2-yl-piperazin-1-yl)-ethyl]-amide (compound 108) was obtained. M+H=380

(J) Proceeding as set forth in Example 28(F) above, but substituting 2,3-benzofuran-2-carboxylic acid for 1-methyl-3-phenyl-1H-thieno[2,3-c]pyrazole-5-carboxylic acid, the compound 2,3-benzofuran-2-carboxylic acid [1-methyl-2-(4-pyrimidin-2-yl-piperazin-1-yl)-ethyl]-amide (compound 109) was obtained. M+H=366

(K) Proceeding as set forth in Example 28(F) above, but substituting 4,6-diphenyl-pyrimidine-2-carboxylic acid for 1-methyl-3-phenyl-1H-thieno[2,3-c]pyrazole-5-carboxylic acid, the compound 4,6-diphenylpyrimidine-2-carboxylic acid [1-methyl-2-(4-pyrimidin-2-yl-piperazin-1-yl)-ethyl]-amide (compound 104) was obtained. M+H=480

(L) Proceeding as set forth in Example 28(F) above, but substituting 5,7-dimethyl-pyrazolo[1,5-a]pyrimidine-3-carboxylic acid for 1-methyl-3-phenyl-1H-thieno[2,3-c]pyrazole-5-carboxylic acid, the compound 5,7-dimethyl-pyrazolo[1,5-a]pyrimidine-3-carboxylic acid [1-methyl-2-(4-pyrimidin-2-yl-piperazin-1-yl)-ethyl]-amide (compound 110) was obtained. M+H=395

(M) Proceeding as set forth in Example 28(F) above, but substituting 5-(2-chlorobenzyl)-4-oxo-4,5,6,7-tetrahydropyrazolo[1,5-a]pyrazine-2-carboxylic acid for 1-methyl-3-phenyl-1H-thieno[2,3-c]pyrazole-5-carboxylic acid, the compound 5-(2-chlorobenzyl)-4-oxo-4,5,6,7-tetrahydropyrazolo[1,5-a]pyrazine-2-carboxylic acid [1-methyl-2-(4-pyrimidin-2-yl-piperazin-1-yl)-ethyl]-amide (compound 119) was obtained. M+H=509

Example 32

Preparation of 2-(2-fluorophenyl)-pyridine-4-carboxylic acid [1-methyl-2-(4-pyrimidin-2-yl-piperazin-1-yl)-ethyl]-amide (A) To a solution of 48% HBr (50 ml) was added 2-aminopicoline (10.0 g, 92.5 mmol) in portions with vigorous stirring between 20° C. to 30° C. After addition, the mixture was cooled to −20° C., and cold Br$_2$ (13 ml, 254 mmol) was added dropwise, maintaining the temperature at −20° C. The resulting paste was kept at −20° C. with hand stirring for 70 minutes, followed by the dropwise addition of a solution of sodium nitrite (17 g, 246 mmol) in water (30 ml) at −20° C. The mixture was warmed to 15° C. over 2 hours, then cooled back to −20° C., treated with cold NaOH (67 g in 120 ml water), maintaining the temperature below −10° C. during addition, the mixture was allowed to warm to RT overnight. The reaction mixture was then partitioned between EtOAc and water, the organic phase washed with brine, dried over anhydrous sodium sulfate, decanted, and the organic solution concentrated under reduced pressure. The residue was purified by silica gel chromatography (20%, 40% EtOAc in hexane) to provide 2-bromo-4-methylpyridine (intermediate XXXIIa, 12.65 g, 79%) as a yellow oil. MW+1=172.

(B) To a solution of intermediate XXXIIa (1 g) and 2-fluorophenyl boronic acid (1.5 g) in diglyme/EtOH (21 ml of 20:1) was added a solution of Na$_2$CO$_3$ (sat'd, 3 ml), followed by tetrakis(triphenylphosphine) palladium (0) (0.2 g). The mixture was heated at 88° C. for 4 h, cooled to RT, and purified to provide 2-(2-fluorophenyl)-4-methylpyridine (intermediate XXXIIb, 0.97 g).

(C) To a suspension of intermediate XXXIIb (0.44 g, 2.35 mmol) in water (25 ml) was added KMnO$_4$ (0.82 g, 5.18 mmol) in two portions, the mixture heated at reflux for 20 h, cooled to RT. The resulting solid was filtered through celite, washed with water and EtOAc, and the two phases separated. The pH of aqueous solution was adjusted to 3, and the white precipitate that formed was isolated and dried to yield 2-(2-fluorophenyl)-pyridine-4-carboxylic acid (intermediate XXXIIc, 0.17 g, 33%). MW+1:218, MW−1:216.

(D) Proceeding as set forth in Example 21(F), but substituting intermediate XXXIIc for intermediate XXIe, the compound 2-(2-fluorophenyl)-pyridine-4-carboxylic acid [1-methyl-2-(4-pyrimidin-2-yl-piperazin-1-yl)-ethyl]-amide (compound 118) was obtained.

(E) Proceeding as set forth in Example 28(F), but substituting 2,6-diphenyl-pyridine-4-carboxylic acid for 1-Methyl-3-phenyl-1H-thieno[2,3-c]pyrazole-5-carboxylic acid, the compound 2,6-diphenyl-pyridine-4-carboxylic acid [1-methyl-2-(4-pyrimidin-2-yl-piperazin-1-yl)-ethyl]-amide (compound 111) was obtained. M+H=479

(F) Similarly, proceeding as set forth in part (E) above, but substituting [1-methyl-2-(4-acetyl-piperazin-1-yl)-ethyl]-amine for intermediate XIIId, the compound 2,6-diphenyl-pyridine-4-carboxylic acid [1-methyl-2-(4-acetyl-piperazin-1-yl)-ethyl]-amide (compound 117) was obtained. M+H=443

(G) Similarly, proceeding as set forth in part (E) above, but substituting 2-chloro-6-(4-methoxyphenyl)-pyridine-4-carboxylic acid for 2,6-diphenyl-pyridine-4-carboxylic acid, the compound 2-chloro-6-(4-methoxyphenyl)-pyridine-4-carboxylic acid [1-methyl-2-(4-pyrimidin-2-yl-piperazin-1-yl)-ethyl]-amide (compound 112) was obtained. M+H=467

(H) Similarly, proceeding as set forth in part (E) above, but substituting 2-chloro-6-(2-methoxyphenyl)-pyridine-4-carboxylic acid for 2,6-diphenyl-pyridine-4-carboxylic acid, the compound 2-chloro-6-(2-methoxyphenyl)-pyridine-4-carboxylic acid [1-methyl-2-(4-pyrimidin-2-yl-piperazin-1-yl)-ethyl]-amide (compound 113) was obtained. M+H=467

(I) Similarly, proceeding as set forth in part (E) above, but substituting 2-chloro-6-(2-methylphenyl)-pyridine-4-carboxylic acid for 2,6-diphenyl-pyridine-4-carboxylic acid, the compound 2-chloro-6-(2-methylphenyl)-pyridine-4-carboxylic acid [1-methyl-2-(4-pyrimidin-2-yl-piperazin-1-yl)-ethyl]-amide (compound 114) was obtained. M+H=451

(J) Similarly, proceeding as set forth in part (E) above, but substituting 2-chloro-6-(thiophen-2-yl)-pyridine-4-carboxylic acid for intermediate 2,6-diphenyl-pyridine-4-carboxylic acid, the compound 2-chloro-6-(thiophen-2-yl)-pyridine-4-carboxylic acid [1-methyl-2-(4-pyrimidin-2-yl-piperazin-1-yl)-ethyl]-amide (compound 115) was obtained. M+H=443

(K) Similarly, proceeding as set forth in part (E) above, but substituting 2-chloro-6-(4-methyl-thiophen-2-yl)-pyridine-4-carboxylic acid for 2,6-diphenyl-pyridine-4-carboxylic acid, the compound 2-chloro-6-(4-methyl-thiophen-2-yl)-pyridine-4-carboxylic acid [1-methyl-2-(4-pyrimidin-2-yl-piperazin-1-yl)-ethyl]-amide (compound 116) was obtained. M+H=457

(L) Similarly, proceeding as set forth in part (E) above, but substituting 5-(thiophen-2-yl)-nicotinic acid for 2,6-diphenyl-pyridine-4-carboxylic acid, the compound 5-(thiophen-2-yl)-nicotinic acid [1-methyl-2-(4-pyrimidin-2-yl-piperazin-1-yl)-ethyl]-amide (compound 121) was obtained. M+H=409

(M) Similarly, proceeding as set forth in part (E) above, but substituting 1,3-diphenyl-pyrimidine-4-carboxylic acid for 2,6-diphenyl-pyridine-4-carboxylic acid, the compound 1,3-diphenyl-pyrimidine-4-carboxylic acid [1-methyl-2-(4-pyrimidin-2-yl-piperazin-1-yl)-ethyl]-amide (compound 120) was obtained. M+H=480

(N) Similarly, proceeding as set forth in part (E) above but substituting 3-cyclopropyl-imidazo[1,5-a]pyridine-1-carboxylic acid for 2,6-diphenyl-pyridine-4-carboxylic acid, the compound 3-cyclopropyl-imidazo[1,5-a]pyridine-1-carboxylic acid [1-methyl-2-(4-pyrimidin-2-yl-piperazin-1-yl)-ethyl]-amide (compound 122) was obtained. M+H=406

(O) Similarly, proceeding as set forth in part (E) above, but substituting 3-ethyl-imidazo-[1,5-a]pyridine-1-carboxylic acid for 2,6-diphenyl-pyridine-4-carboxylic acid, the compound 3-ethyl-imidazo[1,5-a]pyridine-1-carboxylic acid [1-methyl-2-(4-pyrimidin-2-yl-piperazin-1)-ethyl]-amide (compound 123) was obtained. M+H=394

(P) Similarly, proceeding as set forth in part (E) above, but substituting 3-(2-methyl-propyl)-imidazo[1,5-a]pyridine-1-carboxylic acid for 2,6-diphenyl-pyridine-4-carboxylic acid, the compound 3-(2-methylpropyl)-imidazo[1,5-a]pyridine-1-carboxylic acid [1-methyl-2-(4-pyrimidin-2-yl-piperazin-1-yl)-ethyl]-amide (compound 124) was obtained. M+H=422

(Q) Similarly, proceeding as set forth in part (E) above, but substituting 3-cyclopentyl-imidazo[1,5-a]pyridine-1-carboxylic acid for 2,6-diphenyl-pyridine-4-carboxylic acid, the compound 3-cyclopentyl-imidazo[1,5-a]pyridine-1-carboxylic acid [1-methyl-2-(4-pyrimidin-2-yl-piperazin-1-yl)-ethyl]-amide (compound 125) was obtained. M+H=434

(R) Similarly, proceeding as set forth in part (E) above, but substituting 3-(pyridin-2-yl)-imidazo[1,5-a]pyridine-1-carboxylic acid for 2,6-diphenyl-pyridine-4-carboxylic acid, the compound 3-(pyridin-2-yl)-imidazo[1,5-a]pyridine-1-carboxylic acid [1-methyl-2-(4-pyrimidin-2-yl-piperazin-1-yl)-ethyl]-amide (compound 126) was obtained. M+H=443

(S) Similarly, proceeding as set forth in part (E) above, but substituting 3-phenyl-imidazo[1,5-a]pyridine-1-carboxylic acid for 2,6-diphenyl-pyridine-4-carboxylic acid, the compound 3-phenyl-imidazo[1,5-a]pyridine-1-carboxylic acid [1-methyl-2-(4-pyrimidin-2-yl-piperazin-1-yl)-ethyl]-amide (compound 127) was obtained. M+H=442

(T) Similarly, proceeding as set forth in part (E) above, but substituting 1-butyl-5-fluoro-1H-indole-3-carboxylic acid for 2,6-diphenyl-pyridine-4-carboxylic acid, the compound 1-butyl-5-fluoro-1H-indole-3-carboxylic acid [1-methyl-2-(4-pyrimidin-2-yl-piperazin-1-yl)-ethyl]-amide (compound 128) was obtained. M+H=439

Example 33

Preparation of 3,5-di(4-fluorophenyl)benzoic acid [1-methyl-2-(4-pyrimidin-2-yl-piperazin-1-yl)-ethyl]-amide (A) To a solution of methyl 3,5-dibromobenzoate (3.00 g, 10.2 mmol) and 4-fluoro-phenyl boronic acid (1.43 g, 10.2 mmol) in 2-methoxyethyl ether (60 ml) and ethanol (3 ml) was added $Na_2CO_3$ (saturated, 9 ml), followed by tetrakis(triphenylphosphine) palladium (0) (0.2 g). The mixture was heated at 88° C. for 1.5 h, then cooled to room temperature, partitioned between hexane and water, and the organic phase washed with brine, dried over anhydrous sodium sulfate, decanted, and the organic solution concentrated under reduced pressure. The residue was purified by silica gel chromatography (1% EtOAc in hexane) to yield methyl 3-bromo-5-(4-fluorophenyl)benzoate (intermediate XXXIVa, 0.725 g, 23%) as a white solid, and methyl 3,5-di(4-fluorophenyl)benzoate (intermediate XXXIVb, 0.128 g, 4%) as a white solid.

(B) A solution of intermediate XXXIVb (0.31 g, 0.956 mmol) in THF (5 ml) and NaOH (0.3 g in 5 ml of water) was heated at 70° C. for 3 h. After most of THF had evaporated, the aqueous solution was adjusted to pH<1, and the resulting white solid was collected and washed with more water, dissolved in EtOAc, dried over anhydrous sodium sulfate, decanted, and concentrated under reduced pressure to provide 3,5-di(4-fluorophenyl)benzoic acid (intermediate XXXIVc, 0.3 g, 100%) as a white solid. MW−1=309.

(C) Proceeding as set forth in Example 21(F), but substituting intermediate XXXIVc for intermediate XXIe, the compound 3,5-di(4-fluorophenyl)benzoic acid [1-methyl-2-(4-pyrimidin-2-yl-piperazin-1-yl)-ethyl]-amide (compound 133) was obtained.

(D) Similarly, proceeding as set forth in (32F), but substituting intermediate XXXIVa for 2,6-diphenyl-pyridine-4-carboxylic acid, the compound 3-bromo-5-(4-fluorophenyl)benzoic acid [1-methyl-2-(4-pyrimidin-2-yl-piperazin-1-yl)-ethyl]-amide (compound 132) was obtained. M+H=462, 464

(E) To a solution of intermediate XXXIVa (0.2 g, 0.65 mmol) in anhydrousDMF (10 ml) was added allytributyltin (0.25 ml, 0.81 mmol) and tetrakis(triphenylphosphine) palladium (0) (0.2 g). The mixture was heated at 80° C. for 24 h. The mixture was then filtered through celite and washed with 50% EtOAc in hexane, the organic phase was washed with water and brine, dried over anhydrous sodium sulfate, decanted, and the organic solution concentrated under reduced pressure. The residue was purified by silica gel chromatography (2% EtOAc in hexane) to yield 5-allyl-4'-fluoro-biphenyl-3-carboxylic acid methyl ester (intermediate XXXIVe, 0.138 g, 78%) as a white solid.

(F) A mixture of intermediate XXXIVe (0.138 g, 0.51 mmol) and 10% Pd/C (0.1 g) in EtOH (10 ml) was stirred at RT under $H_2$ (balloon) for 4 h. The reaction mixture was then filtered through celite, washed with more EtOH, and the combined solvent was concentrated under reduced pressure. The residue was purified by silica gel chromatography (2% EtOAc in hexane) to yield 5-propyl-4'-fluoro-biphenyl-3-carboxylic acid methyl ester (intermediate XXXIVf, 0.124 g, 89%) as a clear oil.

(G) A solution of intermediate XXxIVf (0.12 g, 0.44 mmol) in THF (5 ml) and NaOH (0.12 g in 3 ml of water) was heated at 70° C. for 24 h. After most of the THF had evaporated, the aqueous solution was adjusted to pH<1. The white precipitate that formed was collected and washed with more water, then dissolved in EtOAc, dried over anhydrous sodium sulfate, decanted, and the organic solution concentrated under reduced pressure to provide 5-propyl-4'-fluoro-biphenyl-3-carboxylic acid (intermediate XXXIVg, 0.116 g, 100%), as a white solid. MW−1=258.

(H) Proceeding as set forth in part (D) above, but substituting intermediate XXXIVg for intermediate XXXIVa, the compound 5-propyl-4'-fluoro-biphenyl-3-carboxylic acid [1-methyl-2-(4-acetyl-piperazin-1-yl)-ethyl]-amide (compound 131) was obtained. MW+1=426.

(I) Proceeding as set forth in part (C) above, but substituting [1-methyl-2-(4-acetyl-piperazin-1-yl)-ethyl]-amine for [1-methyl-2-(4-pyrimidin-2-yl-piperazin-1-yl)-ethyl]-amine, the compound 3,5-di(4-fluorophenyl)benzoic acid [1-methyl-2-(4-acetyl-piperazin-1-yl)-ethyl]-amide (compound 130) was obtained. M+H=478

(J) To a solution of 3-bromo-5-nitro benzoic acid (1 g, 4.06 mmol) and 2-fluoro-phenyl boronic acid (569 mg, 4.06 mmol) in dimethoxyethane (20 ml) and EtOH (1 ml) was added $Na_2CO_3$ (7 ml saturated solution) and palladium tetrakis(triphenylphosphine) (94 mg, 0.08 mmol). The mixture was heated at reflux for 4 h and then stirred at RT for 16 h. The grey precipitate that formed was filtered off and washed with $CH_2Cl_2$. The filtrate was evaporated, affording 3-nitro-5-(2-fluorophenyl)benzoic acid (intermediate XXXIVj, 880 mg, 83% yield) as a white solid. $M^+$=262.

(K) To a solution of intermediate XXXIVj (104 mg, 0.4 mmol) in EtOH (5 ml) was added hydrazine (26 mg, 0.8 mmol) and a catalytic amount of palladium (10%) on carbon.

The reaction mixture was stirred for 18 h at RT and 18 h at reflux. The catalyst was filtered off on a celite pad and washed with warm EtOH. The filtrate was evaporated, affording the product 3-amino-5-(2-fluorophenyl)benzoic acid (intermediate XXXIVk) in quantitative yield as a white solid. M$^+$=232.

(L) A mixture of intermediate XXXIVk (92.4 mg, 0.4 mmol), triethylorthoformate (116 μl, 0.7 mmol) and AcOH (370 μl) was stirred at RT for 18 h. The mixture was evaporated, and to the residue acetic acid (0.5 ml) and NaN$_3$ (104 mg, 1.6 mmol) were added. The reaction mixture was heated at 70° C. for 5 h and stirred at RT for 18 h. Water was added to the reaction, and the product precipitated out as white solid that was washed with water to yield 2'-fluoro-5-tetrazol-1-yl-biphenyl-3-carboxylic acid (intermediate XXXIVl, 52 mg, 48% yield). M$^+$=285.

(M) Proceeding as set forth in part (I) above, but substituting intermediate XXXIVl for intermediate XXXIVc, the compound 2'-fluoro-5-tetrazol-1-yl-biphenyl-3-carboxylic acid [1-methyl-2-(4-acetyl-piperazin-1-yl)-ethyl]-amide (compound 129) was obtained as a yellow foam (11% yield M$^+$=451).

(N) Proceeding as set forth in Example 21(F), but substituting intermediate XXXIVg for intermediate XXIe, the compound 5-propyl-4'-fluoro-biphenyl-3-carboxylic acid [1-methyl-2-(4-pyrimidin-2-yl-piperazin-1-yl)-ethyl]-amide (compound 134) was obtained.

(O) Proceeding as set forth in Example 21(F), but substituting intermediate XXXIVa for intermediate XXIe, the compound 3-bromo-5-(4-fluorophenyl)benzoic acid [1-methyl-2-(4-pyrimidin-2-yl-piperazin-1-yl)-ethyl]-amide (compound 135) was obtained.

(P) Proceeding as set forth in Example 21(F), but substituting 3,5-dibromobenzoic acid for intermediate XXIe, the compound 3,5-dibromobenzoic acid [1-methyl-2-(4-pyrimidin-2-yl-piperazin-1-yl)-ethyl]-amide (compound 136) was obtained.

(Q) Proceeding as set forth in Example 21(F), but substituting 3-(4-fluorophenyl)-benzoic acid for intermediate XXIe, the compound 3-(4-fluorophenyl)-benzoic acid [1-methyl-2-(4-pyrimidin-2-yl-piperazin-1-yl)-ethyl]-amide (compound 137) was obtained.

(R) Proceeding as set forth in (H) above, but substituting 3-(4-fluorophenyl)-benzoic acid for intermediate XXXIVg, the compound 3-(4-fluorophenyl)-benzoic acid [1-methyl-2-(4-pyrimidin-2-yl-piperazin-1-yl)-ethyl]-amide (compound 138) was obtained. M+H=384

Example 34

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
| --- | --- |
| Ingredient | % wt./wt. |
| Active ingredient | 20.0% |
| Lactose | 79.5% |
| Magnesium stearate | 0.5% |

The ingrdients are mixed and dispensed into capsules containing about 100 mg each; one capsule would approximate a total daily dosage.

| Composition for Oral Administration | |
| --- | --- |
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
| --- | --- |
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
| --- | --- |
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
| --- | --- |
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | Grams |
| Active compound | 0.2-2 |
| Span ® 60 | 2 |
| Tween ® 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5% active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 µL of formulation per actuation. A typical dosing schedule is 2-4 sprays every 4-12 hours.

Example 35

P2X$_3$ FLIPR (Fluorometric Imaging Plate Reader) Assay

CHO-K1 cells were transfected with cloned rat P2X$_3$ receptor subunits and passaged in flasks. 18-24 hours before the FLIPR experiment, cells were released from their flasks, centrifuged, and resuspended in nutrient medium at 2.5×10$^5$ cells/ml. The cells were aliquoted into black-walled 96-well plates at a density of 50,000 cells/well and incubated overnight in 5% CO$_2$ at 37° C. On the day of the experiment, cells were washed in FLIPR buffer (calcium- and magnesium-free Hank's balanced salt solution, 10 mM HEPES, 2 mM CaCl$_2$, 2.5 mM probenecid; FB). Each well received 100 µl FB and 100 µl of the fluorescent dye Fluo-3 AM [2 µM final conc.]. After a 1 hour dye loading incubation at 37° C., the cells were washed 4 times with FB, and a final 75 µl/well FB was left in each well.

Test compounds (dissolved in DMSO at 10 mM and serially diluted with FB) or vehicle were added to each well (25 µl of a 4× solution) and allowed to equilibrate for 20 minutes at room temperature. The plates were then placed in the FLIPR and a baseline fluorescence measurement (excitation at 488 nm and emission at 510-570 nm) was obtained for 10 seconds before a 100 µl/well agonist or vehicle addition. The agonist was a 2× solution of α,β-meATP producing a final concentration of 1 µM (P2X$_3$) or 5 µM (P2X$_{2/3}$). Fluorescence was measured for an additional 2 minutes at 1 second intervals after agonist addition. A final addition of ionomycin (5 µM, final concentration) was made to each well of the FLIPR test plate to establish cell viability and maximum fluorescence of dye-bound cytosolic calcium. Peak fluorescence in response to the addition of α,β-meATP (in the absence and presence of test compounds) was measured and inhibition curves generated using nonlinear regression. PPADS, a standard P2X antagonist, was used as a positive control.

Using the above procedure, compounds of the invention exhibited activity for the P2X$_3$ receptor.

Example 36

In Vivo Assay for Asthma and Lung Function

BALb/cJ mice are immunized with a standard immunization protocol. Briefly, mice (N=8/group) are immunized i.p. with ovalbumin (OVA; 10 µg) in alum on days 0 and 14. Mice are then challenged with aerosolized OVA (5%) on day 21 and 22. Animals receive vehicle (p.o.) or a compound of the invention (100 mg/kg p.o.) all starting on day 20.

Lung function is evaluated on day 23 using the Buxco system to measure PenH in response to an aerosol methacholine challenge. Mice are then euthanized and plasma samples collected at the end of the study.

Example 37

Volume Induced Bladder Contraction Assay

Female Sprague-Dawley rats (200-300 g) were anesthetized with urethane (1.5 g/kg, sc). The animals were tracheotomized, and a carotid artery and femoral vein were cannulated for blood pressure measurement and drug administration, respectively. A laparotomy was performed and the ureters were ligated and transected proximal to the ligation. The external urethral meatus was ligated with silk suture and the urinary bladder was cannulated via the dome for saline infusion and bladder pressure measurement.

Following a 15-30 minute stabilization period the bladder was infused with room temperature saline at 100 µl/min until continuous volume-induced bladder contractions (VIBCs) were observed. The infusion rate was then lowered to 3-5 µl/min for 30 minutes before the bladder was drained and allowed to rest for 30 minutes. All subsequent infusions were performed as indicated except the lower infusion rate was maintained for only 15 minutes instead of 30 minutes. Bladder filling and draining cycles were repeated until the threshold volumes (TV; the volume needed to trigger the first micturition bladder contraction) varied by less than 10% for two consecutive baselines and contraction frequency was within 2 contractions for a 10 minute period following the slower infusion rate. Once reproducible TVs and VIBCs were established the bladder was drained and the animal was dosed with drug or vehicle (0.5 ml/kg, i.v.) 3 minutes prior to the start of the next scheduled infusion.

Example 38

Formalin Pain Assay

Male Sprague Dawley rats (180-220 g) are placed in individual Plexiglas cylinders and allowed to acclimate to the testing environment for 30 min. Vehicle, drug or positive control (morphine 2 mg/kg) is administered subcutaneously at 5 ml/kg. 15 min post dosing, formalin (5% in 50 µl) is injected into plantar surface of the right hind paw using a 26-gauge needle. Rats are immediately put back to the observation chamber. Mirrors placed around the chamber allow unhindered observation of the formalin-injected paw. The duration of nociphensive behavior of each animal is recorded by a blinded observer using an automated behavioral timer. Hindpaw licking and shaking/lifting are recorded separately in 5 min bin, for a total of 60 min. The sum of time spent licking or shaking in seconds from time 0 to 5 min is considered the early phase, whereas the late phase is taken as the sum of seconds spent licking or shaking from 15 to 40 min. A plasma sample is collected.

Example 39

Colon Pain Assay

Adult male Sprague-Dawley rats (350-425 g; Harlan, Indianapolis, Ind.) are housed 1-2 per cage in an animal care facility. Rats are deeply anesthetized with pentobarbital sodium (45 mg/kg) administered intraperitoneally. Electrodes are placed and secured into the external oblique musculature for electromyographic (EMG) recording. Electrode leads are tunneled subcutaneously and exteriorized at the nape of the neck for future access. After surgery, rats are housed separately and allowed to recuperate for 4-5 days prior to testing.

The descending colon and rectum are distended by pressure-controlled inflation of a 7-8 cm-long flexible latex balloon tied around a flexible tube. The balloon is lubricated, inserted into the colon via the anus, and anchored by taping the balloon catheter to the base of the tail. Colorectal distension (CRD) is achieved by opening a solenoid gate to a constant pressure air reservoir. Intracolonic pressure is controlled and continuously monitored by a pressure control device. Response is quantified as the visceromotor response (VMR), a contraction of the abdominal and hindlimb musculature. EMG activity produced by contraction of the external oblique musculature is quantified using Spike2 software (Cambridge Electronic Design). Each distension trial lasts 60 sec, and EMG activity is quantified for 20 sec before distension (baseline), during 20 sec distension, and 20 sec after distention. The increase in total number of recorded counts during distension above baseline is defined as the response. Stable baseline responses to CRD (10, 20, 40 and 80 mmHg, 20 seconds, 4 minutes apart) are obtained in conscious, unsedated rats before any treatment.

Compounds are evaluated for effects on responses to colon distension initially in a model of acute visceral nociception and a model of colon hypersensitivity produced by intracolonic treatment with zymosan (1 mL, 25 mg/mL) instilled into the colon with a gavage needle inserted to a depth of about 6 cm. Experimental groups will consist of 8 rats each.

Acute visceral nociception: For testing effects of drug on acute visceral nociception, 1 of 3 doses of drug, vehicle or positive control (morphine, 2.5 mg/kg) are administered after baseline responses are established; responses to distension are followed over the next 60-90 minutes.

Visceral hypersensitivity: For testing effects of drug or vehicle after intracolonic treatment with zymosan, intracolonic treatment is given after baseline responses are established. Prior to drug testing at 4 hours, responses to distension are assessed to establish the presence of hypersensitivity. In zymosan-treated rats, administration of 1 of 3 doses of drug, vehicle or positive control (morphine, 2.5 mg/kg) are given 4 hours after zymosan treatment and responses to distension followed over the next 60-90 minutes.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of formula I:

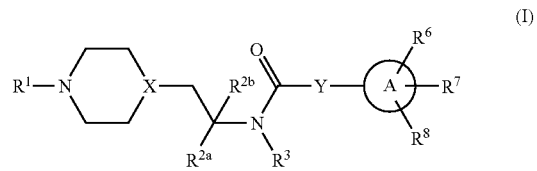

wherein
$R^1$ is —C(=S)CH$_3$, pyridyl, pyrimidinyl, pyrazinyl, thiazolyl, furanyl, acetyl, or carbamoyl;
$R^{2a}$ and $R^{2b}$ are independently H, methyl, or ethyl;
$R^3$ is H or methyl;
Y is a bond, —(CR$^4$R$^5$)$_n$— or —CR$^4$=CR$^5$—; wherein $R^4$ and $R^5$ are each independently H or methyl and n is 1 or 2;
X is N;
A is oxazolyl, thiazolyl, furanyl, pyrazolyl, imidazoly, pyrrolyl, 1H-[1,2,3]triazolyl or 4,5-dihydro-1H-[1,2,4]triazolyl;
$R^6$, $R^7$ and $R^8$ are each independently H, halo, lower alkyl, cycloalkyl, alkylthio, alkylthio-lower alkyl, alkylsulfonyl-lower alkyl, di(lower alkyl)amino-lower alkyl, morpholinyl-lower alkyl, 4-methyl-piperazinyl-methyl, trifluoromethyl, pyridyl, tetrazolyl, thiophenyl, phenyl, biphenyl, or benzyl;
where thiophenyl, phenyl and benzyl are substituted with 0-3 lower alkyl, halo, sulfonamido, trifluoromethyl, lower alkoxy or lower alkylthio;
and pharmaceutically acceptable salts thereof;
wherein when $R^1$ is pyrimidin-2-yl, X is N, Y is a bond and A is oxazol-5-yl the carbon atom at position 4 in said oxazol-5-yl is not substituted by propyl when the carbon atom at position 2 in said oxazol-5-yl is substituted by substituted phenyl and the carbon atom at position 4 in said oxazol-5-yl is not substituted by phenyl when the carbon atom at position 2 is substituted by unsubstituted or substituted phenyl.

2. The compound according to claim 1 wherein Y is a bond.
3. The compound of claim 1, wherein $R^{2a}$ is methyl, $R^{2b}$ is H, and $R^3$ is H.
4. The compound of claim 3, wherein n is 0.
5. The compound of claim 4, wherein A is oxazolyl.
6. The compound of claim 4, wherein $R^6$ is 4-fluorophenyl.
7. The compound of claim 4, wherein $R^7$ is propyl.
8. The compound of claim 7, wherein $R^1$ is pyrimidinyl.
9. The compound of claim 7, wherein $R^1$ is thioacetyl.
10. The compound of claim 7, wherein $R^1$ is pyridyl.
11. The compound of claim 5, wherein $R^6$ is methylthioethyl.
12. The compound of claim 5, wherein $R^6$ is phenyl.
13. The compound of claim 5, wherein $R^6$ is morpholinomethyl.
14. The compound of claim 4, wherein A is thiazolyl.
15. The compound of claim 14, wherein $R^6$ is selected from the group consisting of phenyl, halo-phenyl, alkyl-substituted phenyl, pyridyl, thiophenyl, and trifluoromethyl.

* * * * *